(12) United States Patent
Kan et al.

(10) Patent No.: US 10,980,798 B2
(45) Date of Patent: Apr. 20, 2021

(54) PHARMACEUTICAL COMPOSITIONS OF HYDROPHOBIC CAMPTOTHECIN DERIVATIVES

(71) Applicants: Taiwan Liposome Company, Ltd., Taipei (TW); TLC Biopharmaceuticals, Inc., South San Francisco, CA (US)

(72) Inventors: Pei Kan, Taipei (TW); ChiaHung Hung, Taipei (TW); Keelung Hong, South San Francisco, CA (US); Yun-Long Tseng, Taoyuan (TW); Yung-Hsu Chan, Taipei (TW)

(73) Assignees: TAIWAN LIPOSOME COMPANY, LTD., Taipei (TW); TLC BIOPHARMACEUTICALS, INC., South San Francisco, CA (US)

( * ) Notice: Subject to any disclaimer, the term of this patent is extended or adjusted under 35 U.S.C. 154(b) by 0 days.

(21) Appl. No.: 16/502,946

(22) Filed: Jul. 3, 2019

(65) Prior Publication Data
US 2019/0321356 A1   Oct. 24, 2019

Related U.S. Application Data

(63) Continuation-in-part of application No. 14/353,120, filed as application No. PCT/US2012/063447 on Nov. 2, 2012, now Pat. No. 10,391,056.

(60) Provisional application No. 61/555,084, filed on Nov. 3, 2011.

(51) Int. Cl.
| | | |
|---|---|---|
| A61K 31/4745 | (2006.01) | |
| A61K 47/12 | (2006.01) | |
| A61K 9/107 | (2006.01) | |
| A61K 45/06 | (2006.01) | |
| A61K 47/54 | (2017.01) | |
| A61K 47/10 | (2017.01) | |

(52) U.S. Cl.
CPC ........ *A61K 31/4745* (2013.01); *A61K 9/1075* (2013.01); *A61K 45/06* (2013.01); *A61K 47/10* (2013.01); *A61K 47/12* (2013.01); *A61K 47/544* (2017.08)

(58) Field of Classification Search
None
See application file for complete search history.

(56) References Cited

U.S. PATENT DOCUMENTS

| | | |
|---|---|---|
| 4,166,452 A | 9/1979 | Generales, Jr. |
| 4,256,108 A | 3/1981 | Theeuwes |
| 4,265,874 A | 5/1981 | Bonsen et al. |
| 5,013,556 A | 5/1991 | Woodle et al. |
| 5,731,316 A | 3/1998 | Cao et al. |
| 6,350,756 B1 | 2/2002 | Yang et al. |
| 6,403,604 B1 | 6/2002 | Yang et al. |
| 7,875,602 B2 | 1/2011 | Yang |
| 8,168,648 B2 | 5/2012 | Kuo et al. |
| 2002/0012680 A1 | 1/2002 | Patel et al. |
| 2004/0126886 A1 | 7/2004 | Kan et al. |
| 2004/0247624 A1 | 12/2004 | Unger et al. |
| 2007/0110798 A1* | 5/2007 | Drummond ........ A61K 31/4745 424/450 |
| 2008/0193509 A1 | 8/2008 | Yoshino et al. |
| 2008/0213385 A1 | 9/2008 | Kalb et al. |
| 2009/0285878 A1 | 11/2009 | Hope et al. |
| 2010/0166843 A1 | 7/2010 | Francese et al. |
| 2010/0227877 A1 | 9/2010 | Kuo et al. |
| 2011/0064794 A1 | 3/2011 | Deng et al. |
| 2011/0076308 A1* | 3/2011 | Kwon ................. A61K 31/337 424/400 |
| 2014/0135357 A1 | 5/2014 | Tseng et al. |

FOREIGN PATENT DOCUMENTS

| | | |
|---|---|---|
| CA | 2759060 A1 | 10/2010 |
| CN | 101283983 A | 10/2008 |
| CN | 102018670 A | 4/2011 |
| NZ | 551748 A | 2/2010 |
| WO | 01/85131 A2 | 11/2001 |
| WO | 2007/048002 A2 | 4/2007 |

OTHER PUBLICATIONS

Yang et al (In: Proc Am Assoc Cancer Res; Apr. 18-22, 2009; Denver, CO. Philadelphia (PA): AACR; 2009. Abstract nr 1703). (Year: 2009).*
Bruce et al., "Radiation Sensitization of Micrococcus Radiodurans, Sacino Lutea, and *Escherichia coli* by Hydroxymercuribenzoate," *Radiation Research* 24:473-481, 1965.
Hoskins et al., "Randomized Phase II study of Two Schedules of Topotecan in Previously Treated Patients With Ovarian Cancer: A National Cancer Institute of Canada Clinical Trials Group Study," *Journal of Clinical Oncology* 16:2233-2237, 1998.
Huang et al., "Enhancement of Radiation-induced DNA Damage and Inhibition of Its Repair by a Novel Camptothecin Analog," *Anticancer Research* 30: 937-944, 2010.
Koo et al., "Camptothecin in sterically stabilized phospholipid micelles: A novel nanomedicine," *Nanomedicine: Nanotechnology, Biology, and Medicine* 1: 77-84, 2005.

(Continued)

*Primary Examiner* — Celeste A Roney
(74) *Attorney, Agent, or Firm* — Seed IP Law Group LLP

(57) ABSTRACT

Provide is a method of using a topoisomerase I inhibitor in treatment of cancer to reduce bone marrow suppression. The method includes administering to a subject in need thereof an effective amount of a pharmaceutical composition. The composition has at least one hydrophobic topoisomerase I inhibitor or a pharmaceutically acceptable salt thereof, and at least one polyethylene glycol (PEG) conjugated phospholipid, wherein the molar ratio of said PEG conjugated phospholipid to said hydrophobic topoisomerase I inhibitor or said pharmaceutically acceptable salt of said hydrophobic topoisomerase I inhibitor is about 0.45:1 to about 1.05:1.

18 Claims, 3 Drawing Sheets

(56) References Cited

OTHER PUBLICATIONS

MM de Villiers et al. (eds.), Chapter entitled "Controlled Release and Nanotechnology," *Nanotechnology in Drug Delivery*, p. 289, Dec. 31, 2009.

Oken et al., "Toxicity and response criteria of the Eastern Cooperative Oncology Group," *Am J Clin Oncol* 5: 649-655, 1982.

Sezgin et al., "Preparation and characterization of polymeric micelles for solubilization of poorly soluble anticancer drugs," *European Journal of Pharmaceutics and Biopharmaceutics* 64: 261-268, 2006.

Shenoy et al., "Chemical Radiosensitizers in Cancer Therapy," *Cancer Investigation* 10(6):533-51, 1992.

Watanabe et al., "In vivo antitumor activity of camptothecin incorporated in liposomes formulated with an artificial lipid and human serum albumin," *Journal of Controlled Release 127*: 231-238, 2008.

\* cited by examiner

PHARMACEUTICAL COMPOSITIONS OF HYDROPHOBIC CAMPTOTHECIN DERIVATIVES

CROSS-REFERENCE TO RELATED APPLICATIONS

This application is a continuation-in-part application of U.S. application Ser. No. 14/353,120, filed Apr. 21, 2014, which is a U.S. national phase application of PCT/US2012/063447, filed Nov. 2, 2012, which claims the benefit of U.S. Application No. 61/555,084, filed Nov. 3, 2011. The above-noted applications are incorporated herein by reference in their entity.

FIELD OF INVENTION

The present invention relates to pharmaceutical compositions comprising one or more hydrophobic topoisomerase I inhibitors and methods of their use in treatment of cancer to reduce bone marrow suppression.

BACKGROUND OF THE INVENTION

Topoisomerase I inhibitors are potent anticancer agents that interfere with the topoisomerase I, which is an essential enzyme modifying DNA structure.

Among topoisomerase I inhibitors, camptothecin ((S)-4-ethyl-4-hydroxyl-1H-pyrano-[3'4':6,7]indolizino [1,2-b]quinoline-3,14(4H,12H)-dione)) ("CPT") and its derivatives are known for its broad-spectrum anticancer activities. However, such compounds, as well as many other topoisomerase I inhibitors, have low water solubility, low bioavailability and poor storage stability. In addition, these compounds have severe adverse reactions such as bone marrow suppression, which can result in anemia, neutropenia and/or thrombocytopenia. Therefore, the clinical applications of topoisomerase I inhibitors are limited.

In view of the deficiencies outlined above, there is a need for providing pharmaceutical compositions of topoisomerase I inhibitors with improved drug solubility, extended shelf life and in-use stability and reduced side effects.

BRIEF SUMMARY OF THE INVENTION

The present invention is directed to a method of using a topoisomerase I inhibitor in treatment of cancer to reduce bone marrow suppression, comprising: administering to a subject in need thereof an effective amount of a pharmaceutical composition, which comprises: at least one hydrophobic topoisomerase I inhibitor or a pharmaceutically acceptable salt thereof; and at least one polyethylene glycol (PEG) conjugated phospholipid; wherein the molar ratio of said PEG conjugated phospholipid to said hydrophobic topoisomerase I inhibitor or said pharmaceutically acceptable salt of said hydrophobic topoisomerase I inhibitor is about 0.45:1 to about 1.05:1.

In a particular embodiment, the hydrophobic topoisomerase I inhibitor is selected from the group consisting of: an acridine compound, an actinomycin, an anthracycline compound, an anthraquinone compound, a berberine alkaloid, a benzofluoranthene compound, a benzophenanthridine alkaloid, a camptothecin derivative, a DNA minor groove binder, an indolocarbazole compound, a naphthoquinone compound, a flavonoid, a quinoline compound, a terbenzimidazole compound, and a tricyclic carboxamide derivative.

In a particular embodiment, the hydrophobic topoisomerase I inhibitor is a compound having a water solubility less than camptothecin.

In a particular embodiment, the hydrophobic topoisomerase I inhibitor is a compound having a water solubility less than 0.511 mg/mL.

In a particular embodiment, the pharmaceutical composition further comprising at least one pharmaceutically acceptable excipient or carrier.

In a particular embodiment, the molar ratio of said PEG conjugated phospholipid to said hydrophobic topoisomerase I inhibitor or said pharmaceutically acceptable salt of said hydrophobic topoisomerase I inhibitor is about 0.60:1 to about 1.00:1, preferably about 0.70:1 to about 0.90:1.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Definitions

Figure 1:
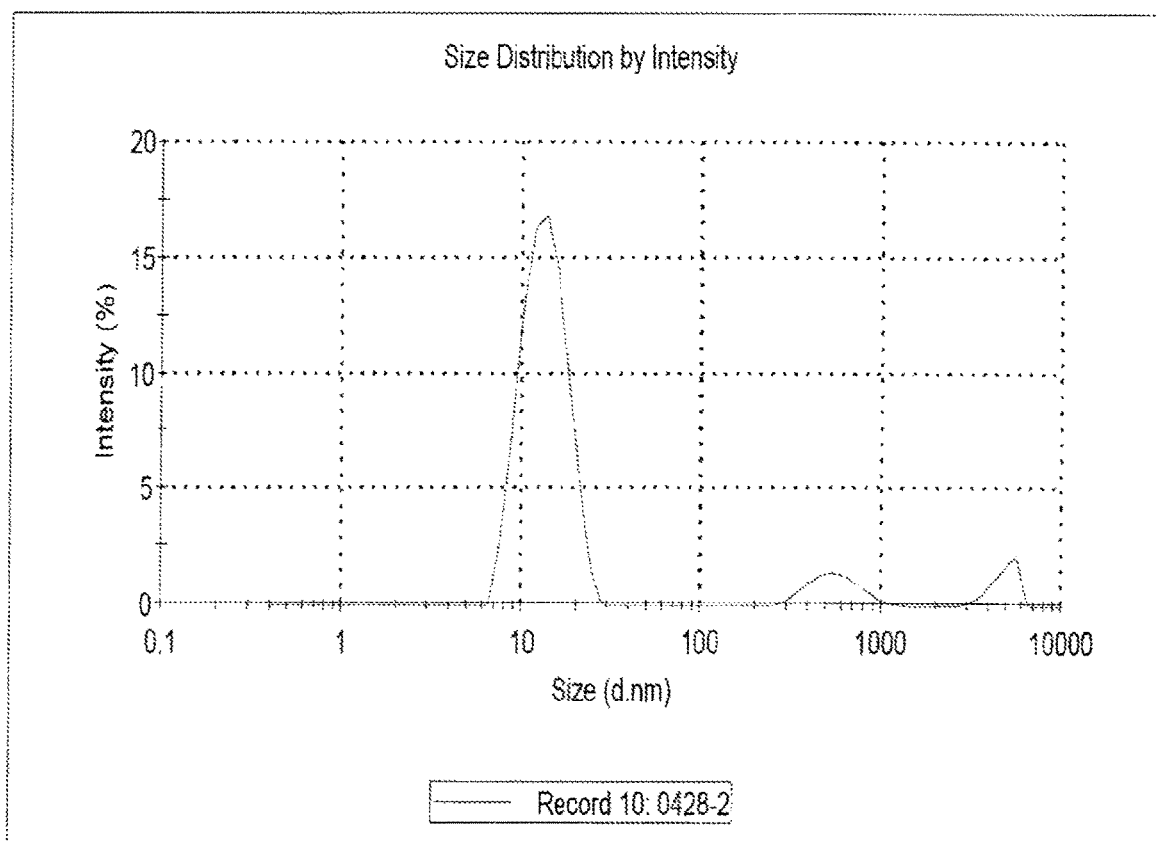
FIG. 1 shows the size distribution of CM315 composition.

As employed above and throughout the disclosure, the following terms, unless otherwise indicated, shall be understood to have the following meanings.

As used herein, the singular forms "a," "an," and "the" include the plural reference unless the context clearly indicates otherwise.

As used herein, the term "about," when referring to a measurable value such as an amount, a temporal duration, and the like, is meant to encompass variations of ±10%, preferably ±5%, more preferably ±1%, and even more preferably ±0.1% from the specified value, as such variations are appropriate to the dose of CPT derivative, unless otherwise specified. As used herein, the term "about," when referring to a range, is meant to encompass variations of ±10% within the difference of the range, preferably ±5%, more preferably ±1%, and even more preferably ±0.1%) from the specified value, as such variations are appropriate to, unless other specified.

"Micelles" are typically defined as spherical receptacles comprised of a single monolayer defining a closed compartment. Generally, amphipathic molecules such as surfactants and fatty acids spontaneously form micellar structures in polar solvents. Micelles typically have a spherical shape with the size of nanometer range. The formation of micelles is driven by decreasing free energy in the system because of removal of hydrophobic fragments from the aqueous environment and the re-establishment of hydrogen bond network with water molecules. In a micelle, there is an arrangement of polar amphipathic molecules, wherein the hydrophilic portion (i.e. heads) of the structure forms the exterior surface and the hydrophobic portion (i.e. tails) resides interiorly, away from the medium. Micelles do not have a bilayer structure and are not considered vesicles or liposomes. The compounds of the invention, when associated with micelles, are either in the compartment, bound to the micelles membrane, or bound to the outside surface of the micelle.

"Pharmaceutical acceptable salt" includes acid addition salts. "Pharmaceutically acceptable acid addition salts" refer to those salts which retain the biological effectiveness and properties of the free bases, which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, trifluoroacetic acid and the like.

An "effective amount," as used herein, includes a dose of the pharmaceutical composition that is sufficient to reduce the symptoms and signs of cancer, such as mass, pain, and weight loss.

The terms "inhibiting" and "suppressing" include slowing or stopping the growth of.

The term "cancer" is to be considered in the broadest general definition as a malignant neoplasm, an abnormal mass of tissue, the growth of which exceeds and is uncoordinated with that of normal tissues and persists in the same excessive manner after cessation of the stimuli that evoked the change. Examples of the types of cancers that may be treated by administrating the formulations of the invention includes, but are not limited to, liver cancer, prostate cancer, colon cancer and glioma.

The term "hydrophobic" includes repelling, or tending not to combine with or incapable of dissolving in, water.

The term "treating," "treated," or "treatment" as used herein includes preventative (e.g. prophylactic), palliative, and curative uses or results. The term "subject" includes a vertebrate having cancer or other diseases. Preferably, the subject is a warm-blooded animal, including mammals, preferably humans.

The term "ionizing radiation" is the one conventionally adopted in the therapeutic field of cancer treatment and includes photons having enough energy for chemical bond ionization such as, for instance, alpha ($\alpha$), beta ($\beta$), and gamma ($\gamma$) rays from radioactive nuclei as well as x-rays. The radiation may be high-LET (linear energy transfer) or low-LET. LET is the energy transferred per unit length of the distance. High LET is said to be densely ionizing radiation and Low LET is said to be sparsely ionizing radiation. Representative examples of high-LET are neutrons and alpha particles. Representative examples of low-LET are x-ray and gamma rays. Low LET radiation including both x-rays and y rays is most commonly used for radiotherapy of cancer patients. The radiation may be used for external radiation therapy that is usually given on an outpatient basis or for internal radiation therapy that uses radiation that is placed very close to or inside the tumor. In case of internal radiation therapy, the radiation source is usually sealed in a small holder called an implant. Implants may be in the form of thin wires, plastic tubes called catheters, ribbons, capsules, or seeds. The implant is put directly into the body. Internal radiation therapy may require a hospital stay. The ionizing radiation source is provided as a unit dose of radiation and is preferably an x-ray tube since it provides many advantages, such as convenient adjustable dosing where the source may be easily turned on and off, minimal disposal problems, and the like. A unit dose of radiation is generally measured in gray (Gy). The ionizing radiation source may also comprise a radioisotope, such as a solid radioisotopic source (e.g., wire, strip, pellet, seed, bead, or the like), or a liquid radioisotopic filled balloon. In the latter case, the balloon has been specially configured to prevent leakage of the radioisotopic material from the balloon into the body lumen or blood stream. Still further, the ionizing radiation source may comprise a receptacle in the catheter body for receiving radioisotopic materials like pellets or liquids. The radioisotopic material may be selected to emit $\alpha$, $\beta$ and $\gamma$. Usually, $\alpha$ and $\beta$ radiations are preferred since they may be quickly absorbed by the surrounding tissue and will not penetrate substantially beyond the wall of the body lumen being treated. Accordingly, incidental irradiation of the heart and other organs adjacent to the treatment region can be substantially eliminated. The total number of units provided will be an amount determined to be therapeutically effective by one skilled in treatment using ionizing radiation. This amount will vary with the subject and the type of malignancy or neoplasm being treated. The amount may vary but a patient may receive a dosage of about 30-75 Gy over several weeks.

The term "alkyl" refers to a monovalent, saturated aliphatic hydrocarbon radical having the indicated number of carbon atoms. For example, a "$C_{1-6}$ alkyl" or an "alkyl of 1-6 carbons" or "Alk 1-6" would refer to any alkyl group containing one to six carbons in the structure. "$C_{1-20}$ alkyl" refers to any alkyl group having one to twenty carbons. Alkyl may be a straight chain (i.e. linear) or a branched chain. Lower alkyl refers to an alkyl of 1-6 carbons. Representative examples of lower alkyl radicals include methyl, ethyl, n-propyl, n-butyl, n-pentyl, n-hexyl, isopropyl, isobutyl, isopentyl, amyl, sec-butyl, tert-butyl, tert-pentyl and the like. Higher alkyl refers to alkyls of seven carbons and above. These include n-heptyl, n-octyl, n-nonyl, n-decyl, n-dodecyl, n-tetradecyl, n-hexadecyl, n-octadecyl, n-eicosyl, and the like, along with branched variations thereof. The radical may be optionally substituted with substituents at positions that do not significantly interfere with the preparation of compounds falling within the scope of this invention and that do not significantly reduce the efficacy of the compounds. The alkyl is optionally substituted with one to five substituents independently selected from the group consisting of halo, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, and lower alkylcarbonylamino.

The term "alkylene" refers to divalent saturated aliphatic hydrocarbyl groups preferably having from 1 to 8 carbon atoms that are either straight-chained (linear) or branched. This term is exemplified by linear groups such as methylene (—CH$_2$—), ethylene (—CH$_2$CH$_2$—), n-propylene (—CH$_2$CH$_2$CH$_2$—) and branched groups such as iso-propylene (—CH$_2$CH(CH$_3$)—) or (—CH(CH$_3$)CH$_2$—) and the like.

The term "alkoxy" refers to a monovalent radical of the formula RO—, where R is an alkyl as defined herein. Lower alkoxy refers to an alkoxy of 1-6 carbon atoms, with higher alkoxy is an alkoxy of seven or more carbon atoms. Representative lower alkoxy radicals include methoxy, ethoxy, n-propoxy, n-butoxy, n-pentyloxy, n-hexyloxy, isopropoxy, isobutoxy, isopentyloxy, amyloxy, sec-butoxy, tert-butoxy, tert-pentyloxy, and the like. Higher alkoxy radicals include those corresponding to the higher alkyl radicals set forth herein. The radical may be optionally substituted with substituents at positions that do not significantly interfere with the preparation of compounds falling within the scope of this invention and that do not significantly reduce the efficacy of the compounds. The alkoxy is optionally substituted with one to five substituents independently selected from the group consisting of halo, lower alkyl, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, and lower alkylcarbonylamino.

The term "cycloalkyl" refers to a monovalent, alicyclic, saturated hydrocarbon radical having three or more carbons forming the ring. While known cycloalkyl compounds may have up to 30 or more carbon atoms, generally there will be three to seven carbons in the ring. The latter include, for example, cyclopropyl, cyclobutyl, cyclopentyl, cyclohexyl, and cycloheptyl. The radical may be optionally substituted with substituents at positions that do not significantly interfere with the preparation of compounds falling within the scope of this invention and that do not significantly reduce the efficacy of the compounds. The cycloalkyl is optionally substituted with one to five substituents independently selected from the group consisting of halo, lower alkyl, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, and lower alkylcarbonylamino.

The term "hydroxycarbonyl" is a monovalent radical having the formula C(O)OH.

The term "lower alkoxycarbonyl" is a monovalent radical having the formula —C(O)OAlk, where Alk is lower alkyl.

The term "lower alkoxycarbonyloxy" is a monovalent radical having the formula —OC(O)OAlk, where Alk is lower alkyl.

The term "sugar" or "sugar residue" refers to a monovalent radical formed by removal of a hydrogen from any hydroxy group of a monosaccharide, disaccharide, oligosaccharide or polysaccharide. The monosaccharide unit that is a part of a disaccharide, oligosaccharide or polysaccharide may be a D or L isomer existing as a five-membered cyclic form (furanose) or a 6-membered cyclic form (pyranose). Representative examples of monosaccharides include glucose, fructose, mannose, and galactose. Representative examples of disaccharides include lactose, maltose, and sucrose. Oligosaccharides may contain 3-20 monosaccharide units linked together, more preferably 3-15 monosaccharide units linked together. Representative examples of oligosaccharides include maltotetraose and cyclodextrin. Representative examples of polysaccharides include amylose, starch and cellulose.

The term "phosphosugar" or "phosphosugar residue" refers to a monovalent radical formed by removal of a hydrogen from any hydroxy group of either a monsaccharide or a phosphoric acid wherein the monosaccharide is linked to the phosphoric acid via an ether linkage. The monosaccharide may be a D or L isomer existing as a five-membered cyclic form (furanose) or a 6-membered cyclic form (pyranose). Representative examples of monosaccharides are set forth above.

The term "lower alkylcarboxyloxy" is a monovalent radical having the formula —OC(O)Alk, where Alk is lower alkyl.

The term "lower alkylcarbonylamino" is a monovalent radical having the formula —NHC(O)Alk, where Alk is lower alkyl.

The term "substituted lower alkyl aminomethyl" is a monovalent radical having the formula —CH$_2$NHAlk, where Alk is a substituted lower alkyl. Representative examples of substituted lower alkyl aminomethyl include (tris(hydroxymethyl)methylamino)methyl, (bis(hydroxymethyl)methylamino)methyl, and (2-hydroxyethylamino) methyl.

A "halo" substituent is a monovalent halogen radical chosen from chloro, bromo, iodo, and fluoro. A "halogenated" compound is one substituted with one or more halo substituents. Chloro is generally preferred.

A "1-naphthyl" or "2-naphthyl" is a radical formed by removal of a hydrogen from the 1- or 2-position of a naphthalene structure, respectively. It is optionally substituted with from one to four substituents independently selected from the group consisting of halo, lower alkyl, lower alkoxy, hydroxy, cyano, nitro, phenyl, amino, halogenated lower alkyl, formyl, halogenated lower alkoxy, hydroxycarbonyl, lower alkoxycarbonyl, lower alkylcarbonyloxy, and lower alkylcarbonylamino.

A "phenyl" is a radical formed by removal of a hydrogen from a benzene ring. The phenyl is optionally substituted with from one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino.

A "cyclic amino" is a monovalent radical of a saturated 5-, 6-, or 7-membered cyclic amine ring having no more than one additional hetero atom such as nitrogen, oxygen, or sulfur. Representative examples include, e.g., 1-pyrrolidino, 1-piperidino, morpholino, piperazino, and the like. These may be substituted or unsubstituted. If substituted, generally they will have no more than 2 substituents chosen from lower alkyl, lower cycloalkyl, hydroxy lower alkyl, phenyl (substituted or unsubstituted), benzyl (substituted or unsubstituted), aminocarbonylmethyl, lower alkylaminocarbonylmethyl, amino, mono- or di-lower alkylamino, or cyclic amino.

"Monovalent radical" refers to attachment of the radical via a single bond.

"Divalent radical" refers to attachment of the radical via a double bond.

"Heteroatom" refers to nitrogen, oxygen, sulfur, or any oxidized form of nitrogen or sulfur.

"Cyano" refers to a monovalent —CN radical.

"Nitro" refers to a monovalent —NO$_2$ radical.

"Amino" refers to a monovalent —NH$_2$ radical.

"Formyl" refers to a monovalent —CHO radical.

"Tri loweralkylsilyl", refers to a monovalent silyl radical substituted with three loweralkyl groups, where the lower alkyl groups may be the same or different.

"Loweralkylcarbonyloxy methyl" refers to a monovalent —CH$_2$C(O) (loweralkyl) radical.

"Substituted vinyl" refers to a substituted —CH═CH$_2$ group were one or more the CH groups are replaced with one to three substituents independently selected from the group consisting of alkyl, halo, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, and lower alkylcarbonylamino.

"Hydroxy" refers to a monovalent OH radical.

"Carbocyclic" refers to a 3-18 membered ring monovalent or divalent radical where all the ring atoms are carbon and may be fully saturated, partially saturated, or unsaturated (i.e., aromatic in nature). The carbocyclic radical is bonded through a saturated, partially saturated, or unsaturated ring via a single or double bond. Carbocyclic groups may be fused, containing 2, 3, or 4 rings where the fused rings are independently saturated, partially saturated, or unsaturated.

Examples of carbocyclic groups include phenyl, naphthyl, fluorenyl, and tetracenyl. The radical may be optionally substituted with substituents at positions that do not significantly interfere with the preparation of compounds falling within the scope of this invention and that do not significantly reduce the efficacy of the compounds. The radical is optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, lower alkylcarbonylamino, sugar residue and phosphosugar residue.

A "carbamoyloxy" is a monovalent radical of the formula $R_{13}R_{14}NC(O)O-$ (i.e. an aminocarbonyloxy) where $R_{13}$ and $R_{14}$ together form a cyclic amino with the nitrogen atom, or each of $R_{13}$ and $R_{14}$ is independently hydrogen, lower alkyl, hydroxy lower alkyl, amino lower alkyl, lower cycloalkyl, phenyl (substituted or unsubstituted), or benzyl (substituted or unsubstituted). Examples include aminocarbonyloxy, methylaminocarbonyloxy, dimethyl aminocarbonyloxy, [4-(1-piperidino)-1-piperidino]carbonyloxy, 1-morpholinocarbonyloxy, 1-pyrrolidinyl, 1-piperazinecarbonyloxy, and others recognized by one skilled in the art or delineated herein.

"Heterocyclic" is a monovalent or divalent radical of a 3-10 membered ring group containing at least one heteroatom in the ring and may be fully saturated, partially saturated, or unsaturated (i.e. aromatic in nature). The heterocycle is bonded through a carbon atom or heteroatom via a single or double bond. The heteroatom in the heterocycle such as N can optionally exist as an N-oxide or S can optionally exist as a sulfoxide or a sulfone.

A "5-membered heterocyclic ring" is a monovalent or a divalent radical of a 5-membered ring containing at least one heteroatom in the ring and may be fully saturated, partially saturated, or unsaturated (i.e. aromatic in nature). Generally, the heterocycle will contain no more than two hetero atoms. The heterocycle is bonded through a carbon atom or heteroatom via a single or double bond. Representative examples of unsaturated 5-membered heterocycles with only one hetero atom include 2- or 3-pyrrolyl, 2- or 3-furanyl, and 2- or 3-thiophenyl. Corresponding partially saturated or fully saturated radicals include 3-pyrrolin-2-yl, 2- or 3-pyrrolidinyl, 2- or 3-tetrahydrofuranyl, and 2- or 3-tetrahydrothiophenyl. Representative unsaturated 5-membered heterocyclic radicals having two hetero atoms include imidazolyl, oxazolyl, thiazolyl, pyrazolyl, and the like. The corresponding fully saturated and partially saturated radicals are also included. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, lower alkylcarbonylamino, sugar residue and phosphosugar residue.

A "6-membered heterocyclic ring" is a monovalent or a divalent radical of a 6-membered ring containing at least one heteroatom and may be fully saturated, partially saturated, or unsaturated (i.e., aromatic in nature). Generally, the heterocycle will contain no more than two hetero atoms. The heterocycle is bonded through a carbon atom or heteroatom via a single or double bond. Representative examples of unsaturated 6-membered heterocycles with only one hetero atom include 2-, 3-, or 4-pyridinyl, 2H-pyranyl, and 4H-pyranyl. Corresponding partially saturated or fully saturated radicals include 2-, 3-, or 4-piperidinyl, 2-, 3-, or 4-tetrahydropyranyl and the like. Representative unsaturated 6-membered heterocyclic radicals having two hetero atoms include 3- or 4-pyridazinyl, 2-, 4-, or 5-pyrimidinyl, 2-pyrazinyl, and the like. The corresponding fully saturated and partially saturated radicals are also included, e.g. 2-piperazine. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, lower alkylcarbonylamino, sugar residue and phosphosugar residue.

A "fused 2-, 3-, or 4-ring heterocyclic" is a monovalent or a divalent radical that is polynuclear in that the adjacent rings share a pair of atoms, generally carbon atoms. At least one of the rings will be heterocyclic in that it will have a noncarbon atom such as nitrogen, oxygen, or sulfur. The ring system may contain from 9 to 18 atoms. The heterocycle is bonded through a carbon atom or heteroatom of one of the rings via a single or double bond. A 2-ring heterocyclic system will generally have 9 or 10 atoms included in the ring. Examples of such a 2-ring system include quinoline, isoquinoline, purine, indolizine, 4H-quinolizine, 3H-pyrrolizine, coumaran, coumarin, isocoumarin, 4-methylcoumarin, 3-chloro-H-methylcoumarin, chromone, benzofuran, benzothiophene, benzothiazole, indole, and the like. A 3-ring system will generally have 12 to 14 atoms included in the ring. Examples of such a 3-ring system include carbazole, acridine, and the like. A 4-ring fused system will generally have 16 to 18 atoms included in the chain. Examples of such a 4-ring system include isothebaine and the like. The radical may be optionally substituted with substituents at positions that do not significantly interfere with the preparation of compounds falling within the scope of this invention and that do not significantly reduce the efficacy of the compounds. The radical is optionally substituted with one to five substituents independently selected from the group consisting of halo, lower alkyl, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, lower alkylcarbonylamino, sugar residue and phosphosugar residue.

Other chemical terms are given their standard meaning as understood by one of skill in the art with guidance from standard texts and dictionaries. Under standard nomenclature used throughout this disclosure, the terminal portion of the substituent is described first, followed by adjacent functionality toward the point of attachment. Thus, for example, a "aminocarbonyl" group refers to a $-C(O)NH_2$ group, a "loweralkoxymethyl" group refers to a $-CH_2$(loweralkoxy) group, a "amino lower alkoxy" group refers to a -(loweralkoxy)amino group, etc.

In one aspect, the present invention provides a pharmaceutical composition comprising a hydrophobic CPT derivative or a pharmaceutically acceptable salt of said CPT derivative, and a polyethylene glycol (PEG) conjugated phospholipid. The PEG moiety has a molecular weight from about 1,000 to about 20,000 daltons and is conjugated to the phospholipid moiety. The PEG conjugated phospholipid is mixed with the CPT derivative or a pharmaceutically acceptable salt of said derivative, at a molar ratio of more than about 0.45:1 to form micelles. The pharmaceutical composition of CPT derivatives of the present invention have uniform micellar size, narrow size distribution, extended storage stability, improved solubility and reduced side effects.

Another aspect of the present invention is directed to methods in inhibiting the growth of cancer cells in a subject, comprises the administration of an effective amount of the pharmaceutical composition described herein to the subject, whereby the symptoms and signs of the cancer in the subject are reduced. The cancer cells in the subject is optionally exposed to one or more anti-cancer agents, include but are not limited to, one or more units dose of radiation, conventional chemotherapy, and targeted cancer therapy.

Topoisomerase I Inhibitors

The term "topoisomerase I inhibitor" as used herein refers to substance which interfere with the action of topoisomerase I, causing DNA damage, inhibition of DNA replication, failure to repair strand breaks, and then, cell death.

In one aspect, the topoisomerase I inhibitors according to the present disclosure include, but not limited to, acridine compounds, actinomycins, anthracycline compounds, anthraquinone compounds, berberine alkaloids, benzofluoranthene compounds, benzophenanthridine alkaloids, camptothecin derivatives, DNA minor groove binders, indolocarbazole compounds, naphthoquinone compounds, flavonoids, quinoline compounds, terbenzimidazole compounds, and tricyclic carboxamide derivatives.

In some embodiments, the topoisomerase I inhibitor according to the present disclosure is selected from the group consisting of aclacinomycin A, 5-acridin-9-ylmethylidene-3-amino-2-thioxothiazolidin-4-one, 5-acridin-9-ylmethylidene-2-thioxoimidazolidin-4-one, 3-acridin-9-ylmethylthiazolidine-2,4-dione, silatecan, 9-aminocamptothecin, gimatecan, karenitecin, diflomotecan, rubitecan, 7-ethylcamptothecin, 10-aminocamptothecin, 10,11-methylenedioxycamptothecin, 9-amino-10,11-methylenedioxycamptothecin, 9-chloro-10,11-methylenedioxycamptothecin, TLC388 HCl, TLC1988 HCl, actinomycin D, NU/ICRF 505, epiberberine, coralyne, beta-lapachone, nitidine, fagaronine, corilagin, rebeccamycin, KT6006, KT6528, ED-110, NB-506, alkannin, shikonin, EMD 21388, EMD 50689, acacetin, kaempferol, saintopin, 5-phenyl-terbenzimidazole (5PTB), topostatin, topostin B567, and intoplicine.

In a particular embodiment, the hydrophobic topoisomerase I inhibitor is a camptothecin derivative having a planar pentacyclic ring structure.

In a particular embodiment, the hydrophobic topoisomerase I inhibitor comprises one or more electron-affinic moieties be directly or indirectly attached to one of the carbons at the $C_5$, $C_7$, $C_9$, $C_{10}$, $C_{11}$, $C_{12}$ or $C_{20}$ position of camptothecin.

In a more particular embodiment, the camptothecin derivative is selected from the group consisting of silatecan, 9-aminocamptothecin, gimatecan, karenitecin, diflomotecan, rubitecan, 7-ethylcamptothecin, 10-aminocamptothecin, 10,11-methylenedioxycamptothecin, 9-amino-10,11-methylenedioxycamptothecin, 9-chloro-10,11-methylenedioxycamptothecin, TLC388 HCl, and TLC1988 HCl.

Camptothecin Derivatives

The camptothecin derivatives, which are suitable for use in the present invention, are hydrophobic camptothecin derivatives. A hydrophobic campthothecin derivative may be formed in a convention manner, for example, by adding a polymer to one or more functional groups of camptothecin ((S)-4-ethyl-4-hydroxyl-1H-pyrano-[3'4':6,7]indolizino[1,2-b]quinoline-3,14(4H,12H)-dione)). The hydrophobic camptothecin derivative can be more or less active than camptothecin. Examples of the CPT derivative include compounds of formulae (I) and (II) in U.S. Pat. No. 7,875,602, which is incorporated herein by reference in its entirety.

The camptothecin derivative of formula (I) is as follows:

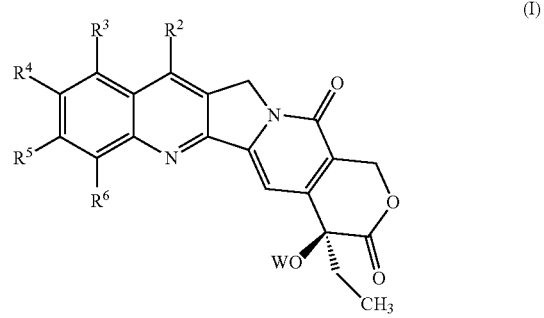

(I)

wherein:

W is alkyl-C(O)—, or $R^1$Y-L-C(O), provided that when W is alkyl-C(O)—, at least one of $R^2$, $R^3$, $R^4$, $R^5$, or $R^6$ is nitro; L is a bond or linear alkylene (1-8) group, optionally substituted with lower alkyl or substituted lower alkyl, wherein one or two methylene (—CH$_2$—) units of the linear alkylene group is optionally replaced with O, S or NH;

Y is =NO—, —N(H)O—, =N—, —R—, O, S, or a bond;

R is H, alkyl, or substituted alkyl;

$R^1$ is optionally substituted carbocyclic, heterocyclic, or fused 2-, 3- or 4-ring heterocyclic;

$R^2$ is hydrogen, halo, lower alkyl, lower alkoxy, hydroxy, $R^Q$Y, R—Y-L-C(O)O—, cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkoxycarbonyloxy, sugar residue, phosphosugar residue residue, O-quinone, substituted lower alkyl aminomethyl, lower alkylcarbonylamino, lower alkylcarbonyloxy methyl, optionally substituted lower alkylcarbonyloxy methyl, substituted vinyl, 1-hydroxy-2-nitroethyl, alkoxycarbonylethyl, aminocarbonyl, alkylcarbonyl, benzoylmethyl, benzylcarbonyloxymethyl, lower alkyliminomethyl or lower alkoxymethyl;

$R^3$ is hydrogen, halo, lower alkyl, lower alkoxy, hydroxy, $R^Q$Y-L-C(0)0-, cyano, nitro, amino, halogenated lower alkyl, halogenated lower alkoxy, hydroxycarbonyl, formyl, lower alkoxycarbonyl, CH$_2$NR$^7$R$^8$ (where each of R$^7$ and R$^8$ is independently H, alkyl of 1-6 carbons, optionally substituted phenyl, hydroxy lower alkyl, amino lower alkyl, or mono- or dialkylamino lower alkyl, or R$^7$ and R$^8$ taken together with —N— represent a cyclic amino-), CH$_2$R$^9$ (where R$^9$ is lower alkoxy, cyano, amino lower alkoxy, mono- or di-lower alkylamino lower alkoxy, lower alkylthio, amino lower alkylthio, or mono- or di-lower alkylamino lower alkylthio), NR$^{10}$R" (where each of R$^{10}$ and R$^{11}$ is independently hydrogen, lower alkyl, phenyl, hydroxy lower alkyl, or amino lower alkyl, or R$^{10}$ and R$^{11}$ taken together with —N— represent a cyclic amino), trialkylsilyl, dialkylamino alkyl, lower alkylcarbonyloxy, lower alkoxycarbonyloxy, sugar residue, phosphosugar residue residue, O-quinone, substituted lower alkyl aminomethyl, or lower alkylcarbonylamino or R³ together with R⁴ is furan, dihydrofuran or 1,4-oxazine-2-one; and R⁴ is hydrogen, halo, lower alkyl, lower alkoxy, hydroxy, R$^Q$Y-L-C(O)O—, cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, lower alkoxycarbonyloxy, sugar residue, phosphosugar residue residue, O-quinone, substituted lower alkyl aminomethyl, or lower alkylcarbonylamino, or R⁴ together with R³ is furan, dihydrofuran or 1,4-oxazine-2-one, or R⁴ together with R⁵ is methylenedioxy;

R⁵ is hydrogen, halo, lower alkyl, lower alkoxy, hydroxy, R$^Q$Y-L-C(O)O—, cyano, nitro, amino, trialkylsilyl, halogenated lower alkyl, halogenated lower alkoxy, hydroxycarbonyl, formyl, lower alkoxycarbonyl, lower alkylcarbonyloxy, lower alkoxycarbonyloxy, sugar residue, phosphosugar residue, O-quinone, substituted lower alkyl aminomethyl, or lower alkylcarbonylamino, or R⁵ together with R⁴ is methylenedioxy;

R⁶ is hydrogen, halo, lower alkyl, lower alkoxy, hydroxy, R$^Q$Y-L-C(O)O—, cyano, nitro, amino, halogenated lower alkyl, halogenated lower alkoxy, hydroxycarbonyl, formyl, lower alkoxycarbonyl, lower alkylcarbonyloxy, lower alkoxycarbonyloxy, sugar residue, phosphosugar residue residue, O-quinone, substituted lower alkyl aminomethyl, or lower alkylcarbonylamino; and R$^Q$ is optionally substituted carbocyclic, heterocyclic, or fused 2-, 3- or 4-ring heterocyclic.

In some embodiments, W is R¹Y-L-(O)—.

R¹ groups that may be incorporated into the active camptothecin derivative as described by Formula (I) include phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperazino, lower alkoxycarbonyl, and lower alkylcarbonylamino; a fused, 2-, 3-, or 4-ring heterocyclic system optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino; 1- or 2-naphthyl optionally substituted with from one to four substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino; or a 5 or 6 membered heterocyclic ring containing one or two nitrogen atoms, which ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino. In a preferred embodiment, R¹ is substituted with at least one carbonyl, amido, trifluoromethyl, halogen, nitro, nitroso, sulfonyl, sulfmyl, phosphoryl, or oxo group. In other embodiments, R¹ is selected from the group consisting of O-quinone, semiquinone, fluorene, imidazole, triazole, pyridine, benzamide, nicotinamide, benzotriazine oxide, furan, thiophene, oxazole, or thiazole, where each of the aforementioned groups may be substituted or unsubstituted.

In other embodiments, R¹ is aromatic.

Preferably at least one of R¹, R², R³, R⁴, R⁵, or R⁶ comprises an electron-affinic moiety, wherein the electron-affinic moiety is a (i) nitro; (ii) carbocyclic or heterocyclic aromatic moiety possessing one or more carbonyl, trifluoromethyl, halogen, nitro, sulfonyl, sulfinyl, phosphoryl, oxide or cyano groups; (iii) heterocyclic aromatic moiety containing two or more heteroatoms; (iv) metal complex; or (v) organo-metallic group in which the metal is covalently bonded to carbon.

Carbocyclic or heterocyclic aromatic electron-affinic moieties contain one to three rings with a total of 5 to 15 ring atoms. The heteroatoms are selected from the group consisting of N, S, O and R Preferably, the carbocyclic or heterocyclic aromatic electron-affinic moieties contain one to two rings with one ring being presently most preferred. Representative carbocyclic aromatic electron-affinic moieties include phenyl and naphthyl groups containing one or more nitro, halogen, carbonyl or sulfonyl substituents, with nitro-substituted phenyl being a preferred carbocyclic aromatic electron-affinic moiety. Representative heterocyclic aromatic electron-affinic moieties include imidazoles, triazoles, pyridines, benzamides, nicotinamides, benzotriazine oxides, furans, thiophenes, oxazoles and thiozoles possessing one or more carbonyl, trifluoromethyl, halogen, nitro, sulfonyl, sulfinyl, phosphoryl, oxide or cyano groups, and preferably at least one nitro group.

Metal complex electron-affinic moieties preferably comprise $Pt^{2+}$, $Co^{3+}$, $Fe^{2+}$, $Fe^{3+}$, $Pd^{2+}$, $Cu^{2+}$, $Ti^{4+}$, or $Zr^{4+}$ as the metal and generally fall into two subgroups: (a) metal complexes of the carbocyclic and heterocyclic aromatic electron-affinic moieties discussed above, and (b) metal complexes of bidentate ligands comprising nitrogen, carbon or sulfur. In general, metal complexes of bidentate ligands correspond to the formula —$BM^LX_K$ wherein B is a bidentate ligand containing nitrogen, carbon or sulfur, $M^L$ is a metal, X is an anionic ligand such as Cl⁻ or ⁻OAc, and k is 1-4.

Organometallic electron-affinic moieties are aliphatic or aromatic mercury radicals. The preparation and use of radiosensitizing agents incorporating mercury containing entities is described in Shenoy et al., *Cancer Investigation*, 10(6):533-551 (1992) and Bruce et al., *Radiation Res.*, 24:473-481 (1965).

Electron-affinic moieties that are particularly suitable for inclusion in the compound of Formula (I) include O-quinone, semiquinone, fluorene, imidazole, triazole, pyridine, benzamide, nicotinamide, benzotriazine oxide, furan, thiophene, oxazole, and thiazole, where each of the aforementioned groups may be substituted or unsubstituted. In a preferred embodiment, R¹ is selected from this group.

In a particularly preferred embodiment, the method of sensitizing tumor cells to radiation is using a camptothecin-based compound selected from the group consisting of:

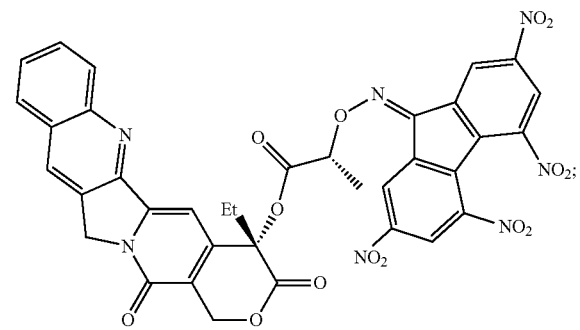

13
-continued
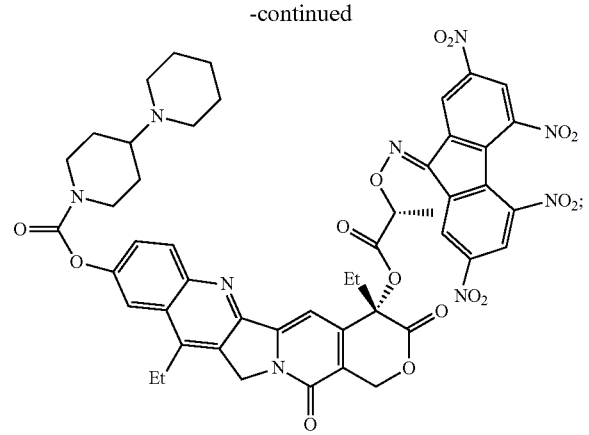
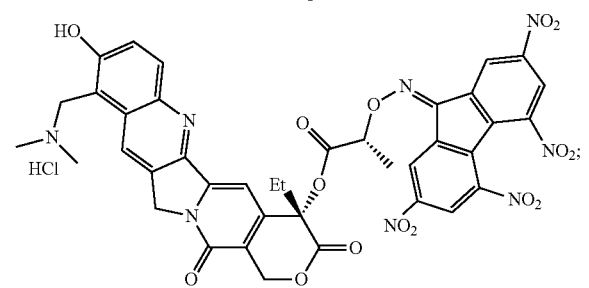
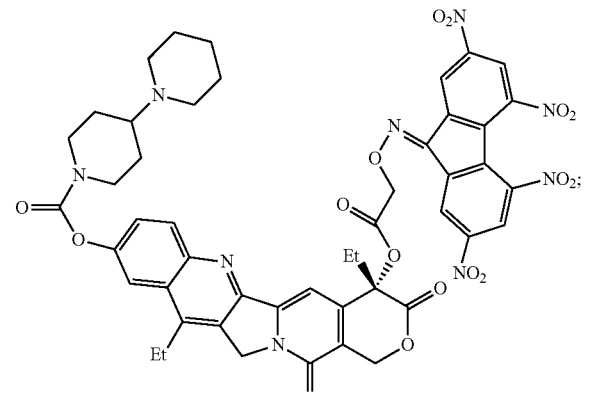
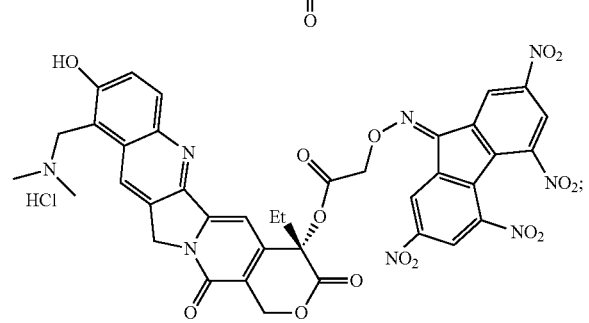
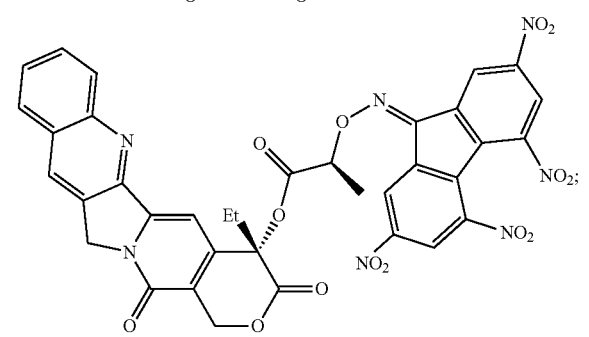
14
-continued
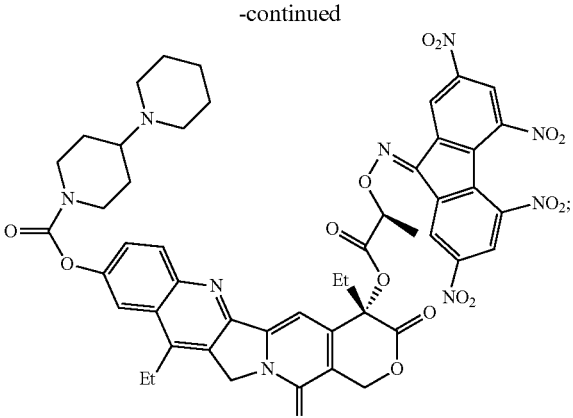
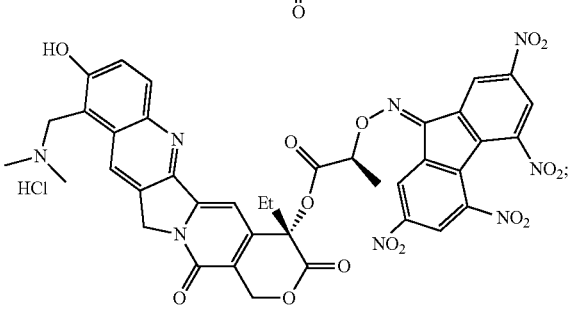
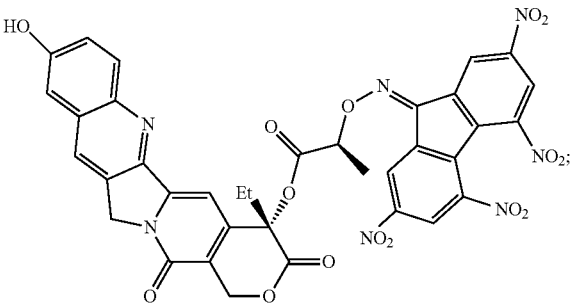
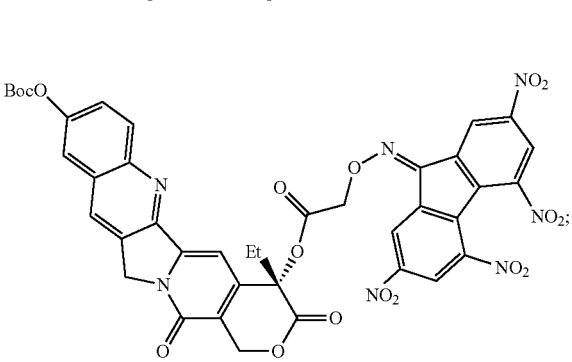
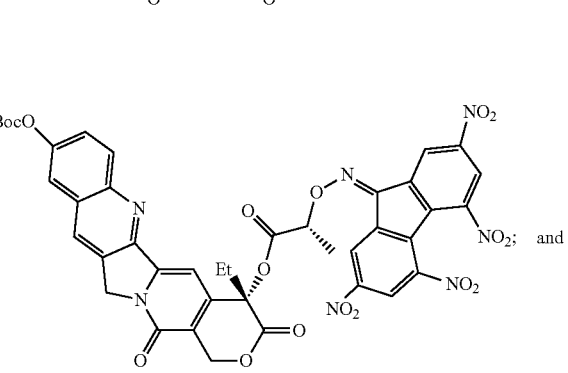
and

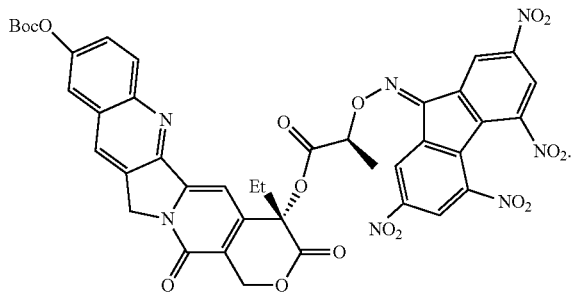

In other embodiments, the electron-affinic moiety includes an $R^1$ that is a 2-nitroimidazol-1-yl or 3-nitro-1,2,4-triazol-1-yl group having the following structure:

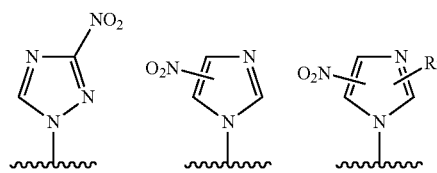

wherein $R^{20}$ is halo, alkyl, or substituted alkyl.

The electron-affinic moieties may be directly attached to one of the carbons at the $C_5$, $C_7$, $C_9$, $C_{10}$, $C_{11}$, $C_{12}$ or $C_{20}$ position of camptothecin or indirectly attached via a linker. While the linker, L, may be any alkylene group of 1 to 8 carbons, optionally interrupted by one or more oxygen, sulfur or nitrogen atoms, a preferred linker is $(CH_2)_m$ or $-(T)_n-X-$, wherein X is O, S, —NR—, or a bond; T is independently CRR'; m is an integer from 0 to 3; n is an integer from 1 to 3, and each of R and R' is independently selected from hydrogen, lower alkyl, and substituted lower alkyl.

In a particularly preferred embodiment, WO—, comprised in the substitution at the −20 position of the camptothecin derivative, is selected from the group consisting of:

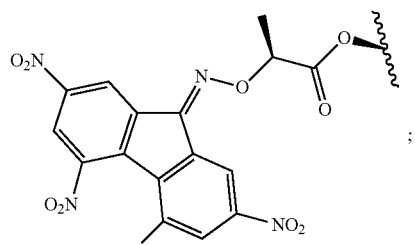

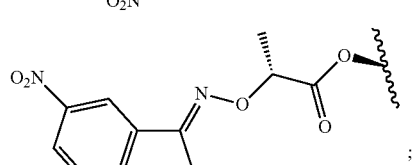

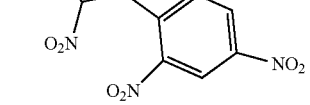

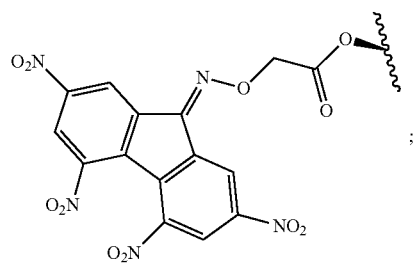

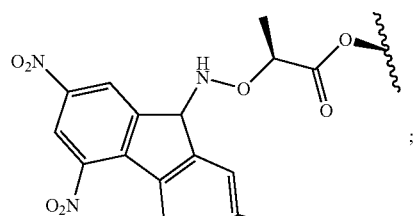

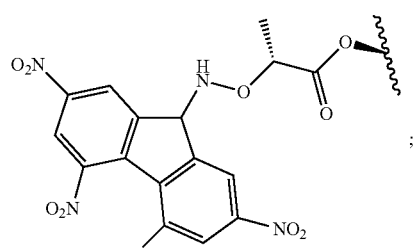

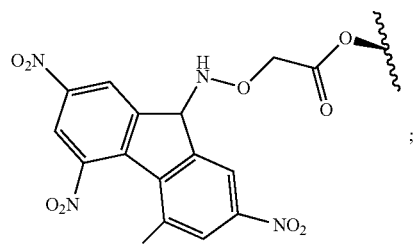

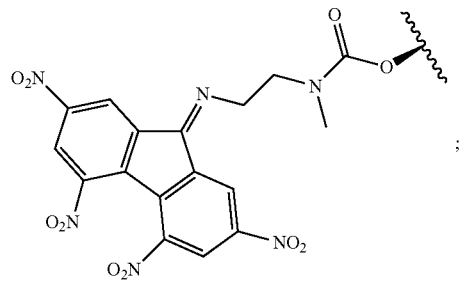

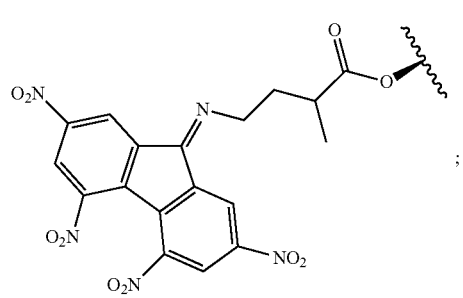

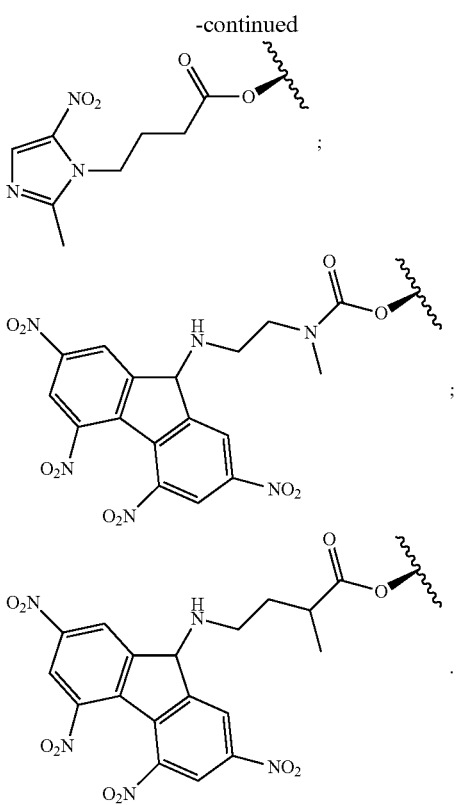

The camptothecin derivative of formula (II) is as follows:

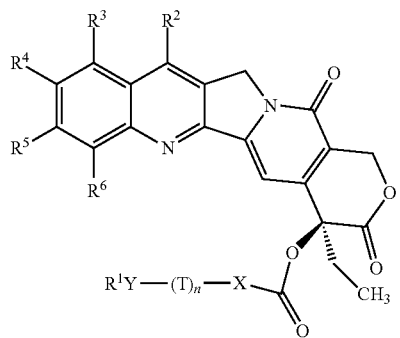

wherein

X is a O, S, —NR—, or a bond; Y is =NO—, —N(H)O—, =N—, —NR—, O, S; or a covalent bond;

T is independently CRR';

each of R and R' is independently selected from hydrogen, $C_{1-4}$ alkyl, and substituted $C_{1-4}$ alkyl;

n is an integer from 0 to 8;

$R^1$ is optionally substituted heterocyclic, aryl, or heteroaryl;

provided that when X is a bond or $CH_2$ and n is 1, 2, or 3, then Y, when bound to $R^1$, is not oxygen; and provided that when X is a bond or $CH_2$, n is 1, 2, or 3; and $R^1$ is heterocyclic containing at least one nitrogen atom, then Y is not bound directly to said nitrogen atom;

$R^2$ is hydrogen, halo, lower alkyl, lower alkoxy, hydroxy, $R^Q$Y-L-C(O)O—, cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkoxycarbonyloxy, sugar residue, phosphosugar residue, O-quinone, substituted lower alkyl aminomethyl, lower alkylcarbonylamino, lower alkylcarbonyloxy methyl, optionally substituted lower alkylcarbonyloxy methyl, substituted vinyl, 1-hydroxy-2-nitroethyl, alkoxycarbonylethyl, aminocarbonyl, alkylcarbonyl, alkylcarbonyloxymethyl, benzoylmethyl, benzylcarbonyloxymethyl, lower alkyliminomethyl or lower alkoxymethyl;

$R^3$ is hydrogen, halo, lower alkyl, lower alkoxy, hydroxy, $R^Q$Y-L-C(O)O—, cyano, nitro, amino, halogenated lower alkyl, halogenated lower alkoxy, hydroxycarbonyl, formyl, lower alkoxycarbonyl, $CH_2NR^7R^8$ (where each of $R^7$ and $R^8$ is independently H, alkyl of 1-6 carbons, optionally substituted phenyl, hydroxy lower alkyl, amino lower alkyl, or mono- or dialkylamino lower alkyl, or and $R^8$ taken together with the nitrogen to which it is attached represent a cyclic amino-), $CH_2R^9$ (where $R^9$ is lower alkoxy, CN, amino lower alkoxy, mono- or di-lower alkylamino lower alkoxy, lower alkylthio, amino lower alkylthio, or mono- or di-lower alkylamino lower alkylthio), $NR^{10}R''$ (where each of $R^{10}$ and $R^{11}$ is independently hydrogen, lower alkyl, phenyl, hydroxy lower alkyl, or amino lower alkyl, or $R^{10}$ and $R^{11}$ taken together with the nitrogen to which they are attached represent a cyclic amino), trialkylsilyl, dialkylamino alkyl, lower alkylcarbonyloxy, lower alkoxycarbonyloxy, sugar residue, phosphosugar residue, O-quinone, substituted lower alkyl aminomethyl, or lower alkylcarbonylamino or $R^3$ together with $R^4$ is furan, dihydro furan or 1,4-oxazine-2-one;

$R^4$ is hydrogen, halo, lower alkyl, lower alkoxy, hydroxy, $R^Q$Y-L-C(O)O—, cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, lower alkoxycarbonyloxy, sugar residue, phosphosugar residue, O-quinone, substituted lower alkyl aminomethyl, or lower alkylcarbonylamino, or $R^4$ together with $R^5$ is methylenedioxy;

$R^5$ is hydrogen, halo, lower alkyl, lower alkoxy, hydroxy, $R^Q$Y-L-C(O)O—, cyano, nitro, amino, halogenated lower alkyl, halogenated lower alkoxy, hydroxycarbonyl, formyl, lower alkoxycarbonyl, lower alkylcarbonyloxy, lower alkoxycarbonyloxy, sugar residue, phosphosugar residue, O-quinone, substituted lower alkyl aminomethyl, or lower alkylcarbonylamino;

$R^6$ is hydrogen, halo, lower alkyl, lower alkoxy, hydroxy, $R^Q$Y-L-C(O)O—, cyano, nitro, amino, trialkylsilyl, halogenated lower alkyl, halogenated lower alkoxy, hydroxycarbonyl, formyl, lower alkoxycarbonyl, lower alkylcarbonyloxy, lower alkoxycarbonyloxy, sugar residue, phosphosugar residue, O-quinone, substituted lower alkyl aminomethyl, or lower alkylcarbonylamino; and $R^Q$ is an optionally substituted heterocyclic, aryl, or heteroaryl group, or $R^1Y$ together form a $NR^aR^b$ group, where $R^a$, $R^b$, and the nitrogen to which they are attached form a cyclic amine or imide ring.

In one embodiment, one of the $R^2$, $R^4$, or $R^5$ is selected from the group consisting of (tris(hydroxymethyl)methylamino)methyl, (bis(hydroxymethyl) methylamino)methyl, and (2-hydroxyethylamino)methyl.

In a preferred embodiment, $R^2$ is selected from the group consisting of (tris(hydroxymethyl)methylamino)methyl, (bis(hydroxymethyl)methylamino)methyl, and (2-hydroxyethylamino)methyl.

In another embodiment, $R^2$ is selected from the group consisting of (tris(hydroxymethyl)methylamino)methyl, (bis(hydroxymethyl)methylamino)methyl, and (2-hydroxyethylamino)methyl; R³ is hydrogen, dimethylamino, amino, or nitro; R⁴ is hydrogen, hydroxy, or 4-(1-piperidino)-1-piperidinocarbonyloxy; or R⁴ together with R⁵ is methylenedioxy; R⁵ is hydrogen; or R⁵ together with R⁴ is methylenedioxy; and R⁶ is hydrogen. In another embodiment, R² is selected from the group consisting of (tris(hydroxymethyl)methylamino)methyl, (bis(hydroxymethyl)methylamino)methyl, and (2-hydroxyethylamino)methyl; R³ is hydrogen; R⁴ together with R⁵ is methylenedioxy and R⁶ is hydrogen.

In yet another embodiment, R² is selected from the group consisting of (tris(hydroxymethyl)methylamino)methyl, (bis(hydroxymethyl)methylamino)methyl, and (2-hydroxyethylamino)methyl and each of R³, R⁴, R⁵, and R⁶ is hydrogen.

In a preferred embodiment R¹ is aromatic.

In a preferred embodiment X is a covalent bond. Additionally, it is preferred that Y is =NO— or —N(H)O— and even more preferably that n is 1 and each of R and R' is independently methyl or hydrogen. In a further preferred embodiment, R¹ is a substituted or unsubstituted carbocyclic, preferably having 1 to 4 aromatic rings. The substituted or unsubstituted carbocyclic may be 9-fluorenyl, preferably substituted with at least one nitro group. In one embodiment of the compound, R¹ is

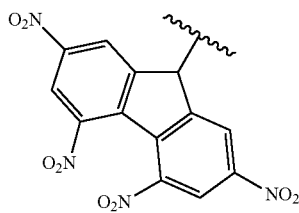 [SMILES: *C1c2cc([N+](=O)[O-])cc([N+](=O)[O-])c2-c2c1cc([N+](=O)[O-])cc2[N+](=O)[O-]]

In a preferred embodiment, the hydrophobic camptothecin derivative is selected from the group consisting of

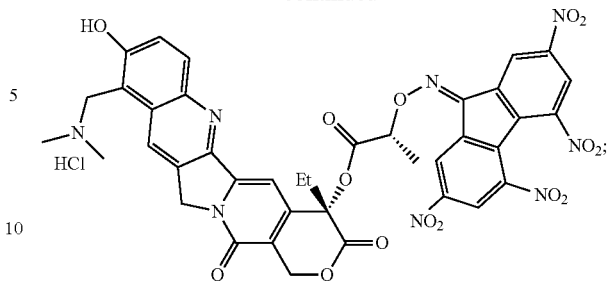

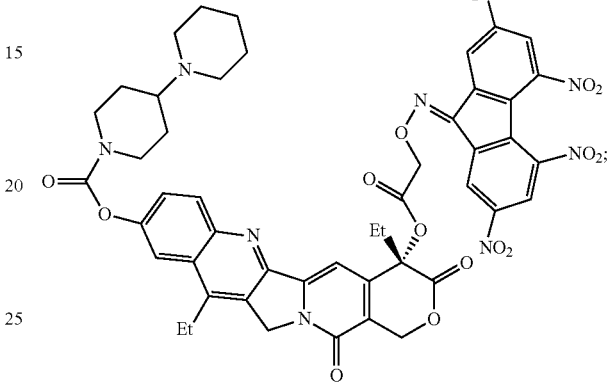

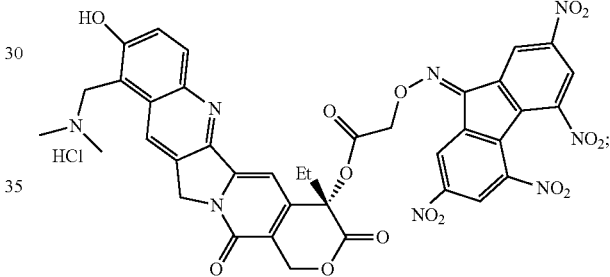

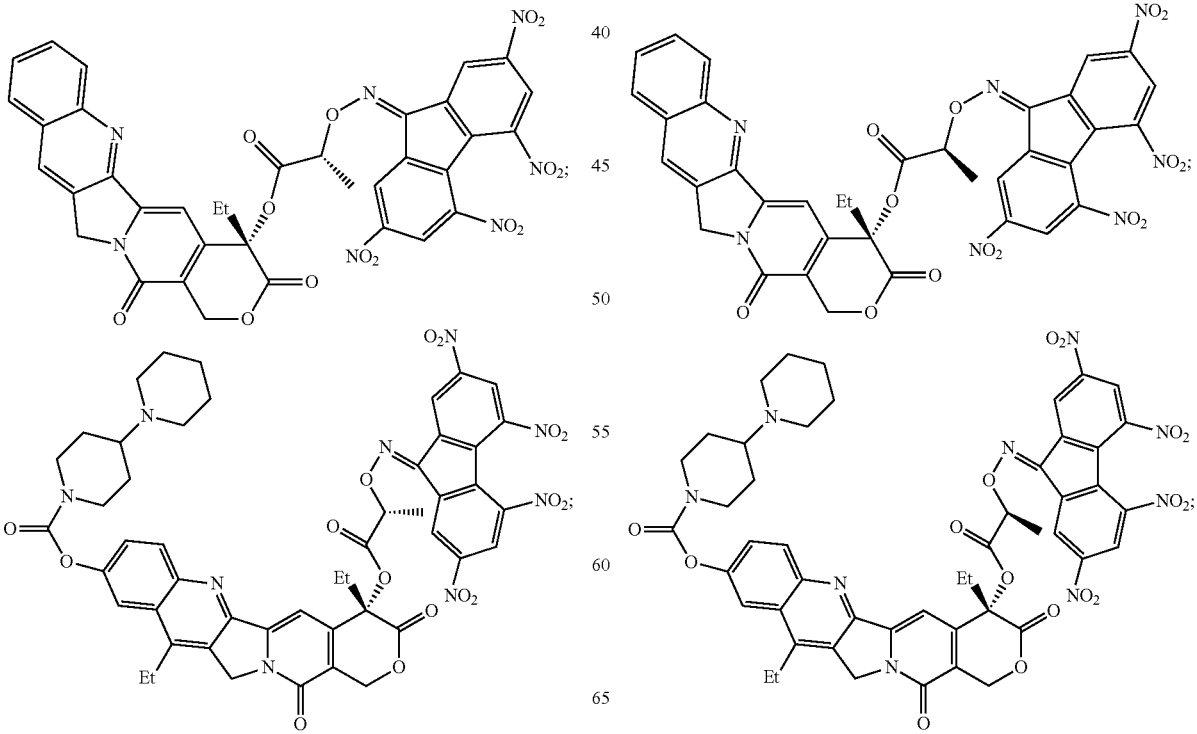

-continued
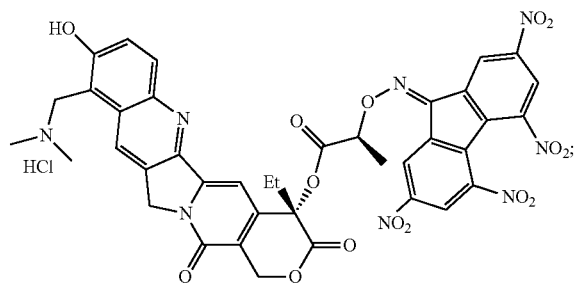 [SMILES: CC[C@@]1(OC(=O)CON=C2c3cc([N+](=O)[O-])cc([N+](=O)[O-])c3-c3c2cc([N+](=O)[O-])cc3[N+](=O)[O-])C(=O)OCc2c1cc1n(c2=O)Cc2cc3c(CN(C)C)c(O)ccc3nc2-1 ; Cl]
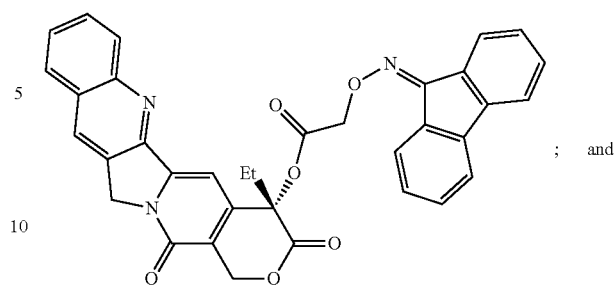
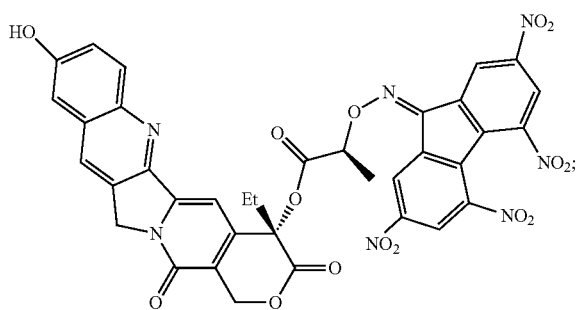
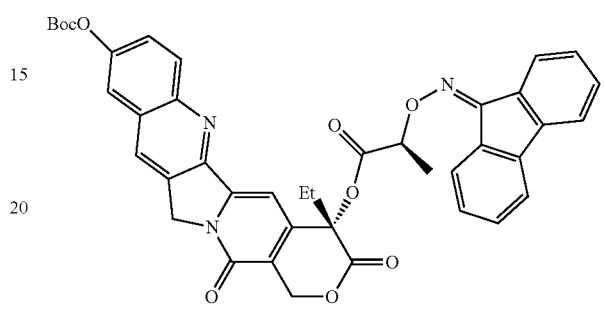
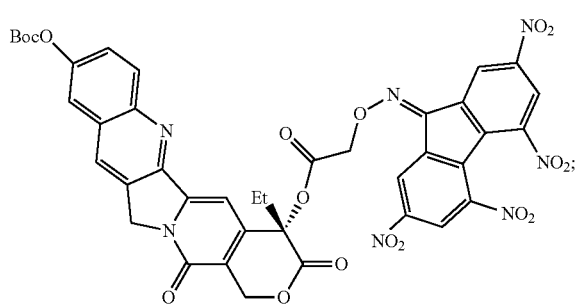
In another preferred embodiment, the compound of Formula (II) includes an $R^1$ or $R^Q$ that is
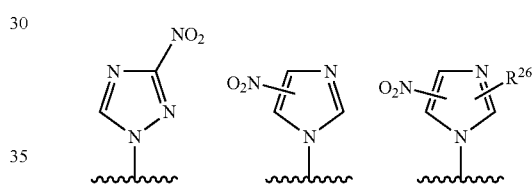
wherein $R^{20}$ is halo, alkyl, or substituted alkyl.
In yet another preferred embodiment of Formula (II), $R^1Y\text{-}(T)_n\text{-}X\text{—}(O)\text{—}$ is
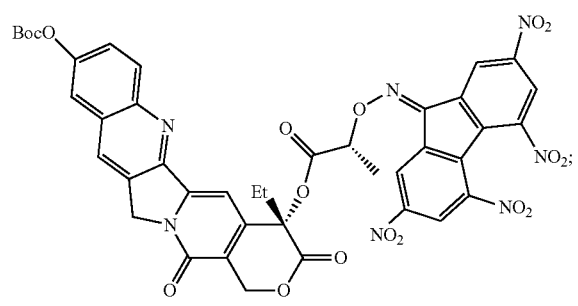
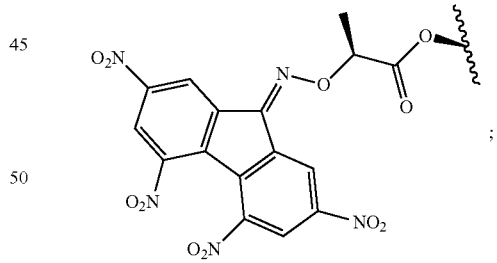
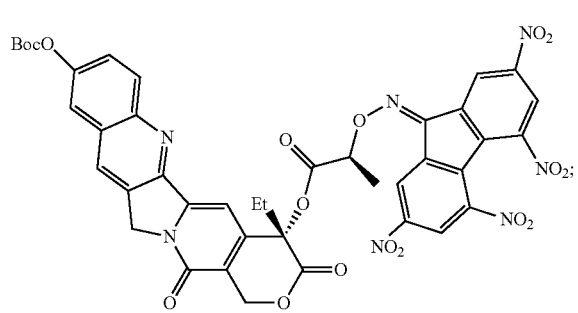
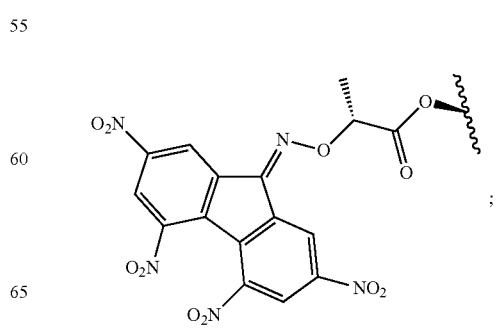

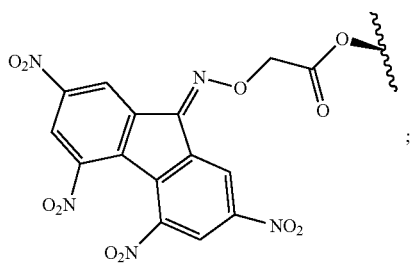

;

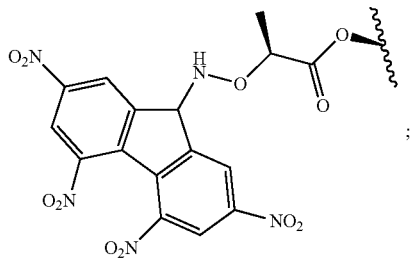

;

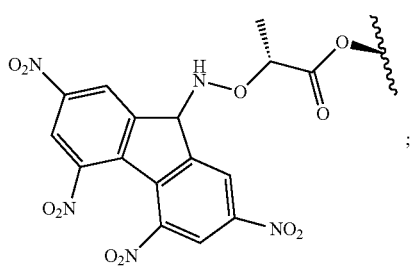

;

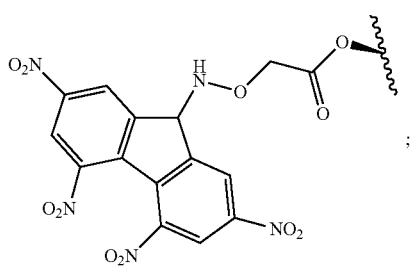

;

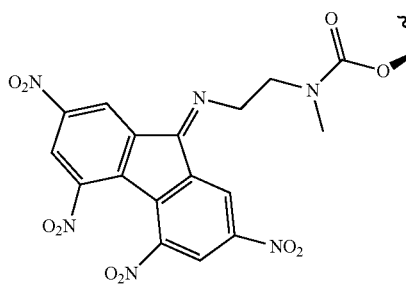

;

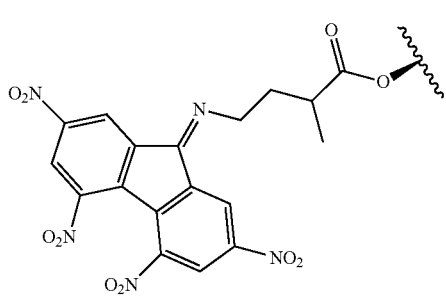

;

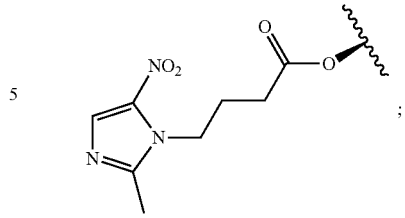

;

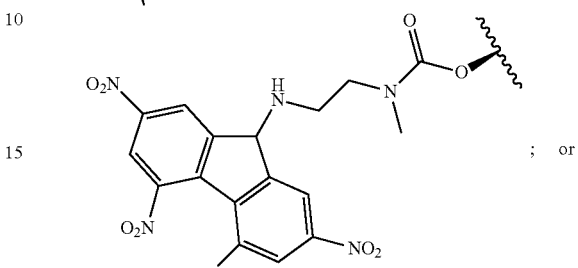

; or

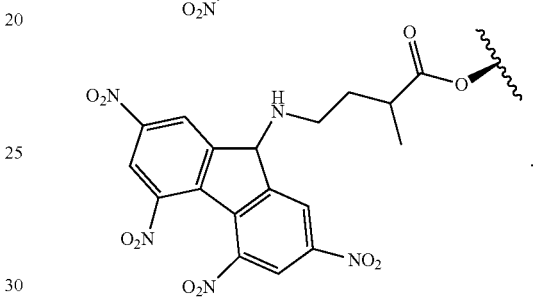

.

Certain CPT derivatives are particularly desirable, for example, a compound of the formula (II), wherein $R^2$ is hydrogen; $R^3$ is $CH_2NR^7R^8$ (where each of $R^7$ and $R^8$ is independently H, alkyl of 1-6 carbons, optionally substituted phenyl, hydroxy lower alkyl, amino lower alkyl, or mono- or dialkylamino lower alkyl, or $R^7$ and $R^8$ taken together with —N— represent a cyclic amino-), $NR^{10}R''$ (where each of $R^{10}$ and $R^{11}$ is independently hydrogen, lower alkyl, phenyl, hydroxy lower alkyl, or amino lower alkyl, or $R^{10}$ and $R^{11}$ taken together with —N— represent a cyclic amino), or dialkylamino alkyl; $R^4$ is lower alkoxy, hydroxy, halogenated lower alkyl, halogenated lower alkoxy, hydroxycarbonyl, formyl, lower alkoxycarbonyl, carbamoyloxy, lower alkylcarbonyloxy, lower alkoxycarbonyloxy, sugar residue, phosphosugar residue, or $R^4$ together with $R^5$ is methylenedioxy; $R^5$ is hydrogen or together with $R^4$ is methylenedioxy; and $R^6$ is hydrogen.

More preferably, $R^3$ is $CH_2NR^7R^8$ (where each of $R^7$ and $R^8$ is lower alkyl), $R^4$ is hydroxy, alkoxy, or alkylcarbonyloxy, and $R^5$ is hydrogen. In a particularly preferred embodiment of this compound, $R^3$ is $CH_2N(CH_3)_2$ and/or $R^4$ is hydroxy.

Similarly, a preferred compound of Formula (II) has the following features: $R^2$ is hydrogen, lower alkyl or halogenated lower alkyl; $R^3$ is hydrogen or lower alkyl; $R^4$ is lower alkoxy, hydroxy, halogenated lower alkoxy, hydroxycarbonyl, carbamoyloxy, lower alkylcarbonyloxy, lower alkoxycarbonyloxy, sugar residue, phosphosugar residue, or $R^4$ together with $R^5$ is methylenedioxy; $R^5$ is hydrogen or together with $R^4$ is methylenedioxy; and $R^6$ is hydrogen.

Preferably, $R^3$ is hydrogen, $R^4$ is carbamoyloxy, and $R^5$ is hydrogen. Even more preferably, $R^2$ is lower alkyl, especially ethyl, and $R^4$ is 4-(1-piperidino)-1-piperidinocarbonyloxy.

In other embodiments of invention, $R^2$ is hydrogen and $R^4$ is 4-(1-piperidino)-1-piperidinocarbonyloxy.

In other embodiments of invention, $R^2$ is hydrogen, $R^3$ is hydrogen and $R^4$ is tert-butoxycarbonyloxy.

Yet another preferred compound of the invention is of Formula (II), wherein $R^2$ is lower alkyl; $R^3$ is hydrogen; $R^4$ is hydroxy, lower alkoxy, halogenated lower alkoxy, hydroxycarbonyl, formyl, lower alkoxycarbonyl, lower alkoxycarbonyloxy, sugar residue, phosphosugar residue, or lower alkylcarbonyloxy; $R^5$ is hydrogen; and $R^6$ is hydrogen.

Preferably, $R^2$ is ethyl and $R^4$ is hydroxy.

Yet another preferred compound of the invention is of Formula (II) where $R^2$, $R^4$, $R^5$ and $R^6$ are hydrogen and $R^3$ is amino or nitro. An alternative compound of Formula (II) has the following substituents: $R^2$ is tri-lower alkylsilyl; $R^3$ is hydrogen; $R^4$ is hydroxy, lower alkoxy, halogenated lower alkoxy, hydroxycarbonyl, formyl, lower alkoxycarbonyl, lower alkoxycarbonyloxy, sugar residue, phosphosugar residue, carbamoyloxy or lower alkylcarbonyloxy; $R^5$ is hydrogen; and $R^6$ is hydrogen. Preferably, $R^2$ is t-butyldimethylsilyl and $R^4$ is hydroxy.

While the linker, L, may be any alkylene group of 1 to 8 carbons, optionally interrupted by one or more oxygen, sulfur or nitrogen atoms, a preferred linker is $(CH_2)_m$ or $-(T)_n-X-$, wherein X is O, S, —NR—, or a bond; T is independently CRR'; m is an integer from 0 to 3; n is an integer from 1 to 3, and each of R and R' is independently selected from hydrogen, alkyl, and substituted alkyl.

In yet another preferred embodiment, the camptothecin derivative of the present invention, known as TLC388 HCl, comprises the following isomers:

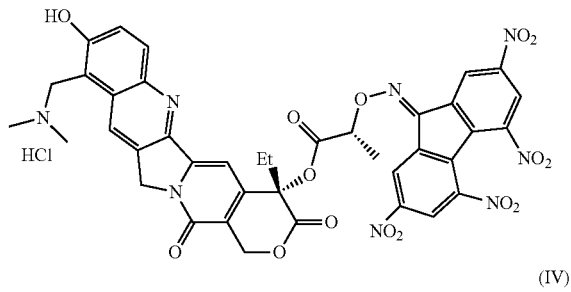

(III)

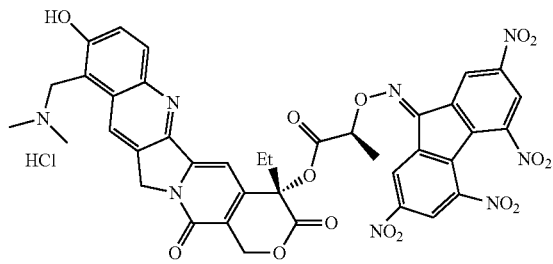

(IV)

TLC388 HCl is a diastereomer and comprises (S,S) and (S,R) isomers in approximately 2:1 molar ratio. As used herein, the term "S" or "R" is a way to name an optical isomer by its configuration, without involving a reference molecule, which is called the R/S system. It labels each chiral center R or S according to a system by which its ligands are each assigned a priority, according to the Cahn Ingold Prelog priority rules, based on atomic number. This system labels each chiral center in a molecule (and also has an extension to chiral molecules not involving chiral centers). If the compound has two chiral centers, it can be labeled, for example, as an (S,S) isomer versus an (S,R) isomer.

The hydrophobic CPT derivatives disclosed herein are prepared by reacting a known camptothecin-based compound having a free hydroxyl or an amine group with an appropriate electron-affinic moiety, by linking the electron-affinic group to any of the $C_5$, $C_7$, $C_9$, $C_{10}$, $C_{11}$, $C_{12}$ or $C_{20}$ carbons of CPT using a variety of methods. Preparation processes of the CPT derivative of the present invention are described in U.S. Pat. No. 7,875,602, which is incorporated herein in its entirety.

In a preferred embodiment, the camptothecin derivative is selected from the group consisting of TLC388 HCl, TLC1988 HCl, and mixtures thereof.

In another group of embodiment, the CPT derivatives include compounds of formula (V), which are disclosed in U.S. Pat. No. 6,350,756, and is incorporated herein by reference in its entirety.

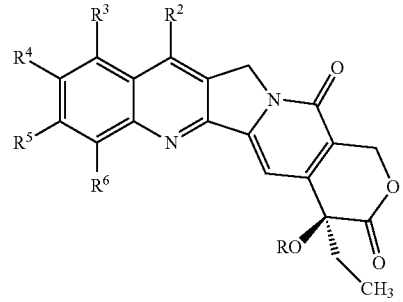

(V)

wherein R is $R^1-O-(CH_2)_m-$, m is an integer of 1-10 and $R^1$ is phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperazino, lower alkoxycarbonyl, and lower alkylcarbonylamino;

a fused, 2-, 3-, or 4-ring heterocyclic system optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

1- or 2-naphthyl optionally substituted with from one to four substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino; a 5 or 6 membered heterocyclic ring containing one or two nitrogen atoms, which ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

$R^2$ is hydrogen, halo, lower alkyl, lower alkoxy, hydroxy, RC(O)O (R is defined hereinbefore), cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkylcarbonylamino, lower alkylcarbonyloxy methyl, substituted vinyl, 1-hydroxy-2-nitroethyl, alkoxycarbonylethyl, aminocarbonyl, alkylcarbonyl, alkylcarbonyloxymethyl, benzoylmethyl, benzylcarbonyloxymethyl, or lower alkoxymethyl;

$R^3$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, $CH_2NR^7R^8$ (where each of $R^7$ and $R^8$ is independently H—, alkyl of 1-6 carbons, optionally substituted phenyl, hydroxy lower alkyl, amino lower alkyl, or mono- or dialkylamino lower alkyl, or $R^7$ and $R^8$ taken together with —N— represent a cyclic amino-), $CH_2R^9$ (where $R^8$ is lower alkoxy, CN, amino lower alkoxy, mono- or di-lower alkylamino lower alkoxy, lower alkylthio, amino lower alkylthio, or mono- or di-lower alkylamino lower alkylthio), or $NR^{10}R''$ (where each of $R^{10}$ and $R^{11}$ is independently hydrogen, lower alkyl, phenyl, hydroxy lower alkyl, or amino lower alkyl, or $R^{10}$ and $R^{11}$ taken together with —N— represent a cyclic amino), dialkylamino alkyl, lower alkylcarbonyloxy lower alkylcarbonylamino; and $R^4$ is hydrogen, halo, lower alkyl, lower alkoxy, hydroxy, RC(O)O (R is defined hereinbefore) cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, or lower alkylcarbonylamino, or $R^4$ together with $R^5$ is methylenedioxy;

$R^5$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, lower alkylcarbonyloxy, or lower alkylcarbonylamino; and $R^6$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, lower alkylcarbonyloxy, or lower alkylcarbonylamino.

In yet another group of embodiment, the CPT derivatives include compounds of formula (VI), which are disclosed in U.S. Pat. No. 6,403,604, and is incorporated herein by reference in its entirety.

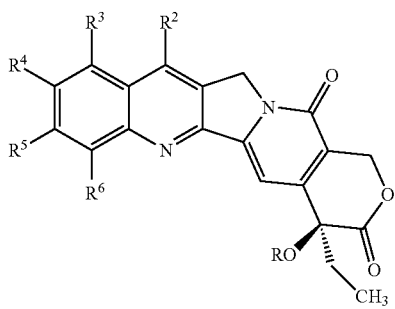

(VI)

wherein R is $R^aR^bN—(CH_2)_m$, m is 2, $R^aR^b$ together with N form (a) a 5-, 6-, or 7-membered cyclic amine having no more than one additional nitrogen, oxygen, or sulfur atom in the ring, which ring is fused to another, carbocyclic ring or rings which resulting fused ring system is optionally substituted with up to two substituents chosen from lower alkyl, lower cycloalkyl, hydroxy lower alkyl, phenyl, substituted phenyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), benzyl, substituted benzyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), aminocarbonylmethyl, lower alkylaminocarbonylmethyl, amino, mono- or di-lower alkyl amino, cyclic amino, or a 5- or 6-membered heterocyclic ring optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino or (b) a 5- or 6-membered cyclic imide ring;

$R^2$ is hydrogen, halo, lower alkyl, lower alkoxy, hydroxy, RC(O)O (R is defined hereinbefore), cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkylcarbonylamino, lower alkylcarbonyloxymethyl, substituted vinyl, 1-hydroxy-2-nitroethyl, alkoxycarbonylethyl, aminocarbonyl, alkylcarbonyl, alkylcarbonyloxymethyl, benzoylmethyl, benzylcarbonyloxymethyl, or lower alkoxymethyl, $R^3$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, $CH_2NR^7R^8$ (where each of $R^7$ and $R^8$ is independently H—, alkyl of 1-6 carbons, optionally substituted phenyl, hydroxy lower alkyl, amino lower alkyl, or mono- or dialkylamino lower alkyl, or $R^7$ and $R^8$ taken together with —N— represent a saturated 5-, 6-, or 7 membered cyclic amine ring having no more than one additional nitrogen, oxygen or sulfur atom that is optionally fused to another carbocyclic ring or rings), $CH_2R^9$ (where $R^9$ is lower alkoxy, CN, amino lower alkoxy, mono- or di-lower alkylamino lower alkoxy, lower alkylthio, amino lower alkylthio, or mono- or di-lower alkylamino lower alkylthio), or $NR^{10}R''$ (where each of $R^{10}$ and $R^{11}$ is independently hydrogen, lower alkyl, phenyl, hydroxy lower alkyl, or amino lower alkyl, or $R^{10}$ and $R^{11}$ taken together with —N— represent a saturated 5-, 6, or 7 membered cyclic amine ring having no more than one additional nitrogen, oxygen or sulfur atom that is optionally fused to another carbocyclic ring or rings), dialkylamino alkyl, lower alkylcarbonyloxy, or lower alkylcarbonylamino; and $R^4$ is hydrogen, halo, lower alkyl, lower alkoxy, hydroxy, RC(O)O (R is defined hereinbefore) cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, or lower alkylcarbonylamino, or $R^4$ together with $R^5$ is methylenedioxy;

$R^5$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, lower alkylcarbonyloxy, or lower alkylcarbonylamino; and R⁶ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, lower alkylcarbonyloxy, or lower alkylcarbonylamino.

In some embodiments, the hydrophobic CPT derivative is a compound selected from the group consisting of: silatecan, 9-aminocamptothecin, gimatecan, karenitecin, diflomotecan, rubitecan, 7-ethylcamptothecin, 10-aminocamptothecin, 10,11-methylenedioxycamptothecin, 9-amino-10,11-methylenedioxycamptothecin, 9-chloro-10,11-methylenedioxycamptothecin, TLC388 HCl, and TLC1988 HCl.

PEG-Conjugated Phospholipid

According to the invention, a PEG conjugated phospholipid, comprising a PEG moiety, preferably having a molecular weight from about 1,000 to about 20,000 daltons and conjugated to a phospholipid moiety, is used as a micelle-forming amphipathic lipid. The PEG conjugated phospholipid is mixed with the topoisomerase I inhibitor or its pharmaceutically acceptable salt to form micelles and stabilizes the topoisomerase I inhibitor or its pharmaceutically acceptable salt. Preferably, the PEG moiety of the PEG conjugated phospholipid has a molecular weight from about 1,000 to about 10,000 daltons. More preferably, the PEG moiety of the PEG conjugated phospholipid has a molecular weight from about 2,000 to about 5,000 daltons. The PEG moiety may be linear, branched (including "dendrimeric" or "star"), and may be derivatized with amino, carboxyl, acyl, sulfonyl, or lower alkoxyl ends e.g. methoxyl polyethylene glycol (mPEG). Combinations of different types of PEG (e.g., branched PEG and linear PEG) may also be used.

The phospholipid moiety of the PEG conjugated phospholipid as used herein may include natural or synthesized phospholipid, for example, phosphatidylethanolamine (such as distearoylphosphatidylethanolamine (DSPE), dipalmitoylphosphatidylethanolamine (DPPE), dioleoylphosphatidylethanolamine (DOPE), 1-palmitoyl-2-oleyl, phosphatidylethanolamine (POPE), and dimyristoylphosphatidylethanolamine (DMPE)); phosphatidylcholine (such as yolk phosphatidylcholine, soy phosphatidylcholine, dipalmitoylphosphatidylcholine (DPPC), distearoylphosphatidylcholine (DSPC), dimyristoylphosphatidylcholine (DMPC), and dioleoylphosphatidylcholine (DOPC)); phosphatidylserine; phosphatidylinositol; sphingophospholipid; hydrogenated phospholipid (such as hydrogenated phosphatidylcholine (HSPC)); and the like; and combinations thereof. Particularly preferred phospholipid for conjugation to PEG as used herein is selected from the group consisting of DSPE, DPPE, DMPE, DOPE, and POPE and combinations thereof.

In one embodiment, the PEG conjugated phospholipid is a PEG-DSPE conjugate, preferably a methoxyl PEG-DSPE conjugate such as 1,2-distearoyl-phosphatidylethanolamine-methyl-polyethyleneglycol-2000 (mPEG2000-DSPE). The chemical structure of mPEG2000-DSPE is shown below:

Pharmaceutical Compositions

The pharmaceutical composition of the present invention comprises at least one hydrophobic topoisomerase I inhibitor or a pharmaceutically acceptable salt thereof; and at least one PEG-conjugated phospholipid. The molar ratio of said PEG conjugated phospholipid to said hydrophobic topoisomerase I inhibitor or said pharmaceutically acceptable salt of said hydrophobic topoisomerase I inhibitor is greater than about 0.45:1.

In a particular embodiment, the pharmaceutical composition of the present invention comprises at least one camptothecin derivative or the pharmaceutically acceptable salt of said derivative; and at least one PEG-conjugated phospholipid. The molar ratio of said PEG conjugated phospholipid to said hydrophobic camptothecin derivative or said pharmaceutically acceptable salt of said hydrophobic camptothecin derivative is greater than about 0.45:1.

Molar Ratio of Phospholipid to Topoisomerase I Inhibitor

The molar ratio of the phospholipid to topoisomerase I inhibitor or its pharmaceutically acceptable salt plays an important role in improving the stability of the topoisomerase I inhibitor or its pharmaceutically acceptable salt in the pharmaceutical composition. In a preferred embodiment, the PEG conjugated phospholipid is mixed with the topoisomerase I inhibitor at a molar ratio (lipid: topoisomerase I inhibitor) more than about 0.45:1. In a more preferred embodiment, the molar ratio of the phospholipid to topoisomerase I inhibitor is from about 0.45:1 to about 1.5:1 and even more preferably, from about 0.45:1 to about 1.05:1. In other embodiments, the molar ratio of the phospholipid to topoisomerase I inhibitor is from about 0.60:1 to about 1.00:1, from about 0.70:1 to about 0.90:1, or from about 0.75:1 to about 1:00:1. By mixing the phospholipid with the topoisomerase I inhibitor at the molar ratio as described herein, the micelles thus formed have an average diameter below about 40 nm, more particularly below about 20 nm, and even more particularly about 15 nm.

In a particular embodiment, the hydrophobic topoisomerase I inhibitor or the pharmaceutically acceptable salt of said hydrophobic topoisomerase I inhibitor and PEG conjugated phospholipid form micelles with a size less than about 40 nm.

pH Adjusting Agent

The pharmaceutical composition of the present invention is preferably acidic. Certain topoisomerase I inhibitors of the present invention, such as TLC388 HCl, may be unstable in an alkaline environment. In a preferred embodiment, the pharmaceutical composition of the present invention has a pH less than about 4.0. In a more preferred embodiment, the pH of the pharmaceutical composition is between about 3 to about 4. The pharmaceutical composition may contain one or more pH adjusting agents to maintain an acidic pH and stabilizing the topoisomerase I inhibitors. The pH adjusting agent can be any pharmaceutical acceptable buffer, which includes one or more of the following: oxalic acid, ethylenediamine tetraacetic acid, maleic acid, aspartic acid, phos-

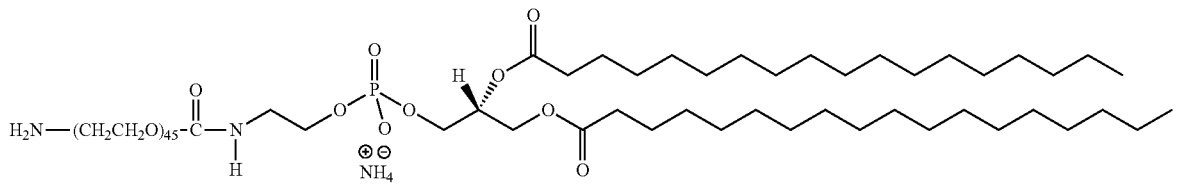

phate, asparagine buffer, glycine, pyruvic acid, pyrophosphate, malonic acid, phthalate, fumaric acid, tartaric acid, citrate, furancarboxylic acid, β-alanine buffer, β:β'-dimethyl glutaric acid, formic acid, lactic acid, γ-aminobutyric acid, barbituric acid, benzoic acid, succinic acid, E-aminocaproic acid, acetic acid, propionic acid, malic acid, pyridine, histidine, cacodylic acid, carbonic acid, hydroxyimidazole, glycerol phosphate, ethylenediamine, imidazole, arsenic acid, 2,4,6-collidine, 1-, 2-, or 4-methyl imidazole, N-ethyl morpholine, veronal, barbital, 2,4-dimethyl imidazole, morpholine, N-ethyl morpholine, 2-amino-2-methyl-1,3-propanediol, 2-amino-2-ethyl-1,3-propanediol, diethanolamine, 4-aminopyridine, serine, boric acid, ammonia, ethanolamine, ephedrine, hydroxyproline, 2-amino-2-methyl-1-propanol, leucine, trimethyl, a-alanine, n-propyl alcohol, methylamine, ethylamine, n-butylamine, triethylamine, dimethylamine, hexamethylenediamine, piperidine, p-toluenesulfonic acid, tris(hydroxymethyl)aminomethane (Tris), glycylglycine, GTA buffer, Good buffer such as MES buffer, Bis-Tris buffer, ADA buffer, PIPES buffer, ACES buffer, MOPSO buffer, BES buffer, MOPS buffer, TES buffer, HEPES buffer, DIPSO buffer, TAPSO buffer, POPSO buffer, HEPPSO buffer, EPPS buffer, Tricine buffer, Bicine buffer, TAPS buffer, CHES buffer, CAPSO buffer, and CAPS buffer. Preferably, the pH adjusting agent comprises one or more of the following: citrate, fumaric acid, diethanolamine, Tris, glycine, acetic acid, succinic acid, tartaric acid, carbonic acid, imidazole and maleic acid.

The pharmaceutical composition of the invention may further comprise at least one cryoprotectant such as mannitol, glycerol, dextrose, sucrose, and/or trehalose. One preferred cryoprotectant is mannitol.

In some embodiments, this invention also provides a pharmaceutical composition further comprising at least one pharmaceutically acceptable excipient, diluent, vehicle, medium for the active ingredient, or a combination.

In one embodiment, the pharmaceutical composition comprising TLC388 HCl or the pharmaceutically acceptable salt of TLC388 HCl; methoxyl PEG-DSPE conjugate; and citric acid, wherein the methoxyl PEG conjugated phospholipid is mixed with the TLC388 HCl or the pharmaceutically acceptable salt of TLC388 HCl at a molar ratio of between about 0.45:1 to about 1.05:1.

Methods for preparing micelles are known in the art, such as the methanol-evaporation method and the co-precipitation method. In the methanol-evaporation method, the topoisomerase I inhibitor and the PEG conjugated phospholipid at a suitable molar ratio, as described herein, are dissolved in methanol. The mixture is then mixed with a suitable buffer solution and the methanol is removed by vacuum evaporation or vice versa; and the mixture is optionally sterilized and/or lyophilized. In the co-precipitation method, the topoisomerase I inhibitor and the PEG conjugated phospholipid at a suitable molar ratio, as described herein, are dissolved in a suitable organic solvent; the mixture is then injected into an anti-solvent to form precipitate and the organic solvent is removed by vacuum drying; the powder thus obtained is dissolved in a suitable buffer solution; and the resulting aqueous solution is optionally sterilized by filtration and/or lyophilized. Details of the preparation are described in the examples below.

The pharmaceutical compositions of the invention may be used in methods to inhibit cancer cells in a subject suffering from a cancer disorder. It is found that the pharmaceutical compositions of the invention inhibit cancer cells and reduce toxicity to normal tissues or cells, particularly bone marrow cells.

The Method of Inhibiting Cancer Cells, Treating Cancer and Reducing Bone Marrow Suppression An aspect of this invention is directed to methods of inhibiting or retarding the growth of cancer cells in a subject, which comprises the administration of an effective amount of the pharmaceutical composition as described herein to the subject, whereby the symptoms and signs of the cancer in the subject are reduced. The method may optionally include the step of exposing the subject's cancer cells to one or more anti-cancer agents, such as ionizing radiation, conventional chemotherapy, or targeted cancer therapy.

Another aspect of this invention is directed to methods of using an topoisomerase I inhibitor in treatment of cancer in a subject to reduce bone marrow suppression, which comprises the administration of an effective amount of the pharmaceutical composition as described herein to the subject, whereby the symptoms and signs of the cancer, as well as the toxicity to bone marrow cells, in the subject are reduced.

The pharmaceutical composition may be constituted into any form suitable for the mode of administration selected. Preferably, the pharmaceutical composition is formulated for parental administration, such as intravenous, intramuscular, subcutaneous and intraperitoneal injection. For example, the pharmaceutical composition of the invention may be in the form of lyophilized powders and further diluted or reconstituted in an aqueous solution such as sterile water, saline or other suitable fluid for injection. Other medically acceptable route of administration includes oral, transdermal, rectal or inhalation and the like.

The dosage of the pharmaceutical composition or the compound of the present invention can be determined by the skilled person in the art according to the embodiments. Unit doses or multiple dose forms are contemplated, each offering advantages in certain clinical settings. According to the present invention, the actual amount of the compound or pharmaceutical composition to be administered can vary in accordance with the age, weight, condition of the subject to be treated and other co-morbidity, and depends on the discretion of medical professionals.

In one embodiment, the method of the present invention comprises co-administering the pharmaceutical composition with one or more anti-cancer agents, such as ionized radiation, targeted cancer therapy such as EGFR and VEGF antagonists, or convention chemotherapy.

Examples of convention chemotherapy include, but are not limited to anthracycline antibiotic, DNA synthesis inhibitor, alkylating agent, antifolate agent, metabolic inhibitor or the like.

Examples of anthracycline antibiotic include, but are not limited to, doxorubicin, Epirubicin, Mitoxantrone and the like.

Examples of DNA synthesis inhibitor include, but are not limited to, mitomycin C, 5-FU (5-fluorouracil), capecitabine, irinotecan hydrochloride, thymitaq and the like.

Examples of alkylating agent include, but are not limited to, cisplatin, carboplatin, oxaliplatin, mitoxantrone and the like.

Examples of metabolic inhibitor include, but are not limited to, etoposide, rottlerin and the like.

Examples of antifolate agent include, but are not limited to, Nolatrexed and the like.

The following examples further illustrate the present invention. These examples are intended merely to be illustrative of the present invention and are not to be construed as being limiting.

EXAMPLE 1
Preparation of the Pharmaceutical Compositions of Camptothecin Derivatives 1.1 Camptothecin Derivatives TLC388 base, with the following formula was used to prepare the pharmaceutical composition:

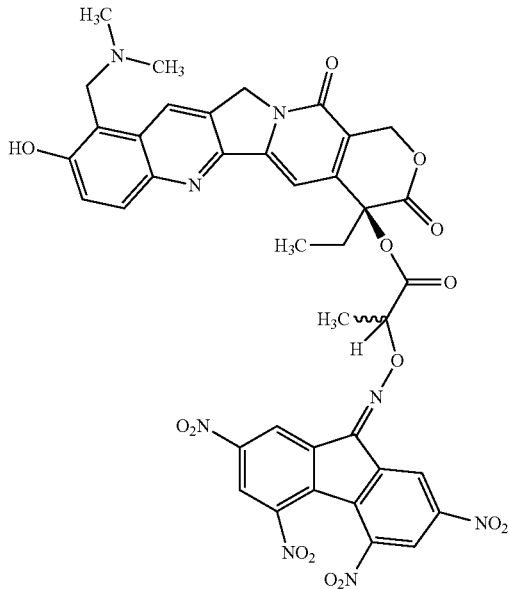 [SMILES: CC[C@@]1(OC(=O)C(C)ON=C2c3cc([N+](=O)[O-])cc([N+](=O)[O-])c3-c3c2cc([N+](=O)[O-])cc3[N+](=O)[O-])C(=O)OCc2c1cc1n(c2=O)Cc2cc3c(CN(C)C)c(O)ccc3nc2-1]

The chemical name of the TLC388 base is (S)-10-[(dimethylamino)methyl]-4-ethyl-9-hydroxy-4-O-[(±)-2-(2",4",5",7"-tetranitro-9"-fluorenylideneaminooxy)propionyl]-1H-pyrano[3',4':6,7]indolizino[1,2-b]quinoline-3,14-(4H,12H)-dione. TLC388 base was used to prepare the pharmaceutical compositions because of its fixed molecular weight, which is 850.7. This allowed for the exact quantitation of the CPT derivative by mole.

TLC1988 HCl, with the following formula, was used to prepare the CM1901 and 1903 pharmaceutical compositions:

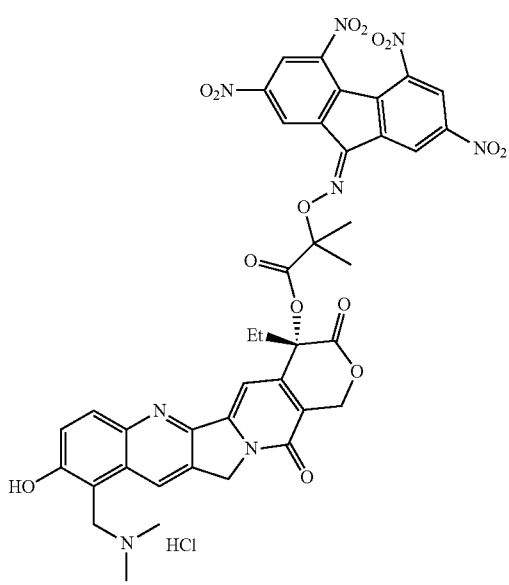

TLC-1988
FW = 864.20
900.18 (as HCl salt)

The chemical name of TLC1988 HCl is (S)-10-[(dimethylamino)methyl]-4-ethyl-9-hydroxy-4-O-[2-methyl-2-(2",4",5",7"-tetranitro-9"-fluorenylideneaminooxy)propionyl]-1H-pyrano[3',4':6,7]indolizino[1,2-b]quinoline-3,14-(4H, 12H)-dione, monohydrochloride.

1.2 Methanol-Evaporation Method

The pharmaceutical compositions were prepared by methanol-evaporation method, as illustrated below:

1. TLC388 base (or TLC1988 HCl) and mPEG2000-DSPE at various molar ratios, as shown in Table 1, were dissolved in methanol;
2. The mixture in Step 1 was mixed with a buffer solution containing mannitol and tartaric acid, at the volume ratio of 1 to 1;
3. The methanol in the mixture in Step 2 was removed by vacuum evaporation, using a rotor bottle in the 50-55° C. water bath (pressure 11-21 cm Hg) for at least 30 minutes;
4. The mixture in Step 3 underwent sterile filtration using a 0.22 μm membrane, followed by lyophilization for subsequent analyses.

An alternative route was carried out in the following order:

1. TLC388 base (or TLC1988 HCl) and mPEG2000-DSPE at various molar ratios were dissolved in methanol;
2. The methanol in the mixture in Step 1 was removed by vacuum evaporation using a rotor bottle in the 50-55° C. water bath (pressure 11-21 cmHg) for at least 30 minutes;
3. The mixture in Step 2 was mixed with a buffer solution containing mannitol and tartaric acid, at the volume ratio of 1 to 1;
4. The mixture in Step 3 underwent sterile filtration using a 0.22 μm membrane, followed by lyophilization for subsequent analyses.

1.3 Co-Precipitation Method

The pharmaceutical compositions were prepared by co-precipitation method, as illustrated below:

1A. TLC388 base and mPEG2000-DSPE at various molar ratios were dissolved in a suitable organic solvent, such as methanol;
2A. The mixture in Step 1A was injected into an anti-solvent to form precipitation;
3A. The mixture in Step 2A underwent filtration and vacuum drying to remove solvent, and intermediate powder was formed;
4A. The intermediate powder in Step 3A was dissolved in a buffer solution containing mannitol and citric acid;
5A. The mixture in Step 4A underwent sterile filtration, followed by lyophilization.

EXAMPLE 2

The Solubility of the Pharmaceutical Composition

The solubility of the pharmaceutical composition in the present invention was evaluated in term of the micellar size and the distribution.

An evaluation of the pharmaceutical composition with various phospholipid to CPT derivative molar ratios was performed. The results of the study are summarized in Table 1.

TABLE 1

The characteristics of the various pharmaceutical compositions with various phospholipid to CPT derivative molar ratios.

| Pharmaceutical Composition | Phospholipid/ CPT derivative | Size (nm) | PI* |
|---|---|---|---|
| CM317 [a] | 0.09/1 | 67.4 | 0.364 |
| CM316 [a] | 0.29/1 | 87.2 | 0.824 |
| CM315 [a] | 0.45/1 | 21.9 | 0.263 |
| CM314 [a] | 0.68/1 | 13.4 | 0.105 |
| CM391 [b] | 0.46/1 | 13.2 | 0.314 |
| CM392 [b] | 0.52/1 | 11.5 | 0.136 |
| CM386 [b] | 0.65/1 | 15.2 | 0.142 |
| CM381 [b] | 0.71/1 | 15.1 | 0.106 |
| CM382 [b] | 0.70/1 | 15.2 | 0.099 |
| CM387 [b] | 0.75/1 | 15.2 | 0.106 |
| CM388 [b] | 0.85/1 | 14.8 | 0.075 |
| CM389 [b] | 0.95/1 | 14.7 | 0.069 |
| CM390 [b] | 1.05/1 | 15.3 | 0.118 |
| CM1901 [a] | 1.25/1 | 15.8 | 0.427 |
| CM1903 [a] | 1.5/1 | 16.4 | 0.236 |

[a] The pharmaceutical composition was prepared by the methanol-evaporation method.
[b] The pharmaceutical composition was prepared by the co-precipitation method.
*PI = Polydispersity, a measure of distribution of particles. High PI means wide size distribution and low PI reflects a good monodispersed particle size.

The micellar size (hydrodynamic diameter) of the pharmaceutical composition was measured by dynamic light scattering (DLS) using a Zetasizer NANO-ZS90 with Zetasizer Software 6.20 (Malvern Instruments). The pharmaceutical composition was diluted with normal saline at ambient temperature to a concentration to provide a Count Rate of 50 to 200 kcps. The Z-average diameter was obtained from three measurements.

The results in Table 1 show that to obtain a micelle size less than 40 nm, the minimum phospholipids to CPT derivative molar ratio is more than about 0.45.

In addition, the aqueous solubility of TLC1988 HCl increased to 10 mg/mL with mPEG2000-DSPE formulation.

An evaluation of the size distribution of the pharmaceutical compositions with various phospholipid to CPT derivative molar ratios was performed. The results are shown in FIGS. 1 and 2.

FIG. 1 shows the size distribution graph of the CM315 Composition. The micellar size of the CM315 Composition is less than 40 nm, and the size distribution graph shows CM315 Composition has a narrow size distribution with one major peak at about 15 nm.

Figure 2:
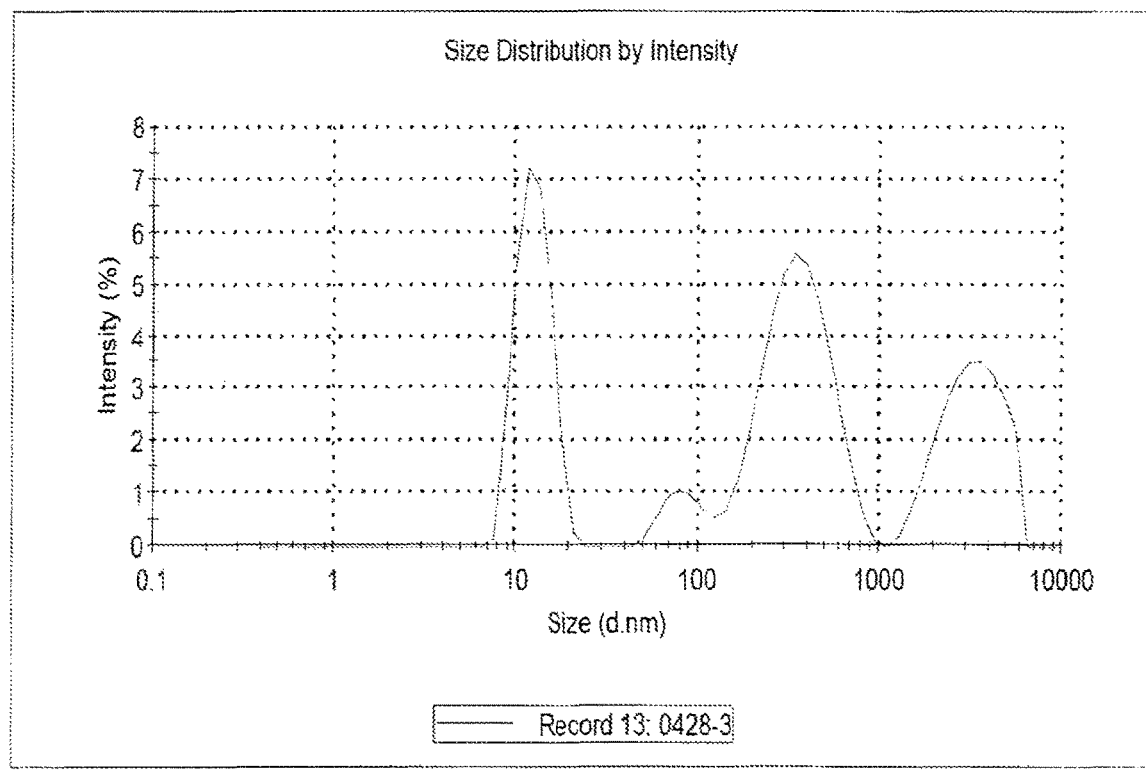
FIG. 2 shows the size distribution of CM316 composition.

FIG. 2 shows the size distribution graph of the CM316 Composition. The micellar size of the CM316 Composition is over 40 nm, and the size distribution graph shows a wide size distribution with multiple peaks. The main peak is at more than 200 nm.

These results show that the pharmaceutical composition with a phospholipid to CPT derivative molar ratio of more than about 0.45 has a micelle size less than 40 nm and narrower size distribution.

EXAMPLE 3

Effect of pH Adjusting Agent and pH on Stability

TLC388 HCl and TLC1988 HCl are known to be unstable in an alkaline condition. An evaluation of various pH adjusting agents and the pH was performed to determine the suitable pH range and the pH adjusting agent for the pharmaceutical composition.

Tartaric acid or citric acid was added to the pharmaceutical compositions and incubated the mixture at 40° C. for 2 weeks. The stability of the pharmaceutical compositions after 2 weeks of incubation is summarized in Tables 2-4.

TABLE 2

The effect of the pH Adjusting Agents and pH on the Stability of the Pharmaceutical Compositions

| Pharmaceutical Composition | Excipient | pH | Stability at 40° C. for 2 weeks | |
|---|---|---|---|---|
| | | | Drug %[c] | Size (nm) |
| CM314-3 [a] | 1.2% mannitol & | 2.95 | 96% | 424.0 |
| CM314-4 [a] | 0.5% tartaric acid/NaOH | 3.78 | 75% | 260.0 |
| CM348-3 [b] | 5% mannitol & | 3.10 | 93% | 16.0 |
| CM348-4 [b] | 0.2% tartaric | 4.00 | 86% | 15.6 |
| CM348-5 [b] | acid/NaOH | 5.01 | 76% | 180.0 |
| CM347-3 [b] | 5% mannitol & | 3.14 | 92% | 24.5 |
| CM347-4 [b] | 0.2% citric | 3.99 | 85% | 14.6 |
| CM347-5 [b] | acid/NaOH | 4.94 | 78% | 225.0 |
| CM381 [b] | 1.5% mannitol & | 3.0 | 99% | 15.2 |
| CM382 [b] | 0.1% citric acid/NaOH | 3.5 | 97% | 15.0 |
| CM1901 [a] | 2% mannitol & | 2.5~3.5 | N/A | N/A |
| CM1903 [a] | 0.2% tartaric acid/NaOH | 2.5~3.5 | N/A | N/A |

[a] The pharmaceutical composition was prepared by the methanol-evaporation method.
[b] The pharmaceutical composition was prepared by the co-precipitation method.
[c] Percentage of remaining TLC388 base with respect to the initial content.

TABLE 3

Accelerated Stability Evaluation of the CM381 Composition (1.5% mannitol + 0.08 sodium citric, PEG Phospholipid/TLC388 = 0.71)

| | 40 ± 2° C. | | |
|---|---|---|---|
| CM381 | Initial | 14 days | 28 days |
| Appearance of cake | Light yellow cake | Light yellow cake | Light yellow cake |
| Clarity | Clear | Clear | Clear |
| pH | 3.10 | 3.11 | 3.30 |
| Size (nm) | 15.1 | 15.2 | 15.2 |
| Distribution (PdI) | 0.106 | 0.064 | 0.037 |
| Conc. (mg/mL) | 8.61 | 8.57 | 8.61 |
| Drug remaining (%)[a] | 100.0% | 99.5% | 100.0% |

[a] Percentage TLC388 remaining with respect to initial content of TLC388.

TABLE 4

Accelerated Stability Evaluation of CM382 Composition (1.5% mannitol + 0.11 sodium citric, PEG phospholipid/TLC388 = 0.7)

| | 40 ± 2° C. | | |
|---|---|---|---|
| CM382 | Initial | 14 days | 28 days |
| Appearance of cake | Light yellow cake | Light yellow cake | Light yellow cake |
| Clarity | Clear | Clear | Clear |
| pH | 3.56 | 3.58 | 3.61 |
| Size (nm) | 15.2 | 15.0 | 15.1 |
| Distribution (PdI) | 0.099 | 0.085 | 0.069 |
| Conc. (mg/mL) | 8.61 | 8.42 | 8.44 |
| Drug remaining (%)[a] | 100.0% | 97.8% | 98.0% |

[a] Percentage TLC388 remaining with respect to initial content of TLC388.

The results show that the suitable pH range for the pharmaceutical compositions of the invention is lower than about pH 4.0. In addition, citric acid and tartaric acid are suitable pH adjusting agents for the pharmaceutical compositions in the present invention.

EXAMPLE 4

Cytotoxicity Assay

4.1 Cell Lines and Culture Conditions

Human hepatoma cell lines Hep3B, HepG2, HepG2/2.2.15, Huh-7 and Sk-Hep-1, human glioblastoma cell line RG-2, and human prostate cancer cell line DU145 were maintained in DMEM (HyClone Laboratories, Logan, Utah, USA). Human prostate cancer cell line LNCap was maintained in RPMI-1640 culture medium (Sigma-Aldrich, St. Louis, Mo., USA). Culture medium was supplemented with 10% heat-inactive fetal bovine serum (HyClone Laboratories, Logan, Utah, USA), 1% penicillin/streptomycin (Invitrogen, Carlsbad, Calif., USA), 1 mM sodium pyruvate (HyClone Laboratories, Logan, Utah, USA) and 1 mM L-Glutamine (HyClone Laboratories, Logan, Utah, USA). Human prostate cancer cell line PC-3 was maintained in the Ham's F-12K medium (Invitrogen, Carlsbad, Calif., USA) with the same medium supplements described in the culture medium except that the fetal bovine serum concentration was reduced to 7% by volume. Cancer cells were maintained at 37° C. in a humidified incubator (Nuaire, USA) containing 5% $CO_2$.

4.2 Sulforhodamine B Assay (SRB Assay)

The SRB assay was used for measuring cancer cell viability. The cancer cells in the plate wells were rinsed with 1× PBS and treated with 1× trypsin-EDTA (Invitrogen, Carlsbad, Calif.). The culture medium was added to dilute the trypsin-EDTA. The detached cancer cells were harvested by centrifugation and suspended in the 1 ml culture medium. Ten μl of the cell suspension was dispensed into counting chambers and the cell density was determined microscopically. The cells in 198 μl suspensions were seeded onto a 96-well cell plate (Nunc, Rochester, N.Y.) at the appropriate cell density per well and incubated in the cell culture incubator overnight.

4.3 Testing Compositions

We evaluated the ant-cancer activity of the following CPT derivatives pharmaceutical compositions:
1. TLC388 HCl, a non-water soluble CPT derivative (obtained from ScinoPharm Taiwan Ltd., Taiwan);
2. Topotecan, a water-soluble CPT derivative and is used as positive control (Commercially available from Wuhan Yuancheng Technology Development Co., Ltd, China); and
3. Lipotecan® (CM382 Composition in Table 1, comprises PEG conjugated phospholipid and CPT derivative at a molar ratio of 0.7).

TLC388 HCl and Topotecan were dissolved in DMSO (Sigma-Aldrich, St. Louis, Mo., USA) and diluted with 5 mM of citric acid (J.T. Baker, NJ, USA) to desired concentrations. Lipotecan® was dissolved with sterile $ddH_2O$ and diluted with 5 mM of citric acid to desired concentration.

The intermediate plate was set up for the drug dilution. 5 mM of citric acid was used for free TLC388 HCl and Topotecan dilution and $ddH_2O$ was used for Lipotecan® dilution. Two μl of free TLC388 HCl or Lipotecan® of the following concentrations were then added to the cells: 0, 0.0008, 0.003, 0.012, 0.049, 0.195, 0.781, 3.125, 12.5 and 50 μmole/ml. Each concentration was tested in triplicate and was incubated at 37° C. with the cancer cells for 24 h, 48 h and 72 h. The highest concentration of DMSO was 0.05% in this test.

At the end of the incubation period, cells were fixed by adding 50 μl of cold 50% TCA (w/v) (Sigma, St Louis, Mo., USA) to a final concentration of 10% TCA and further incubated at 4° C. for 60 minutes. The supernatants were discarded, and the plates were washed five times with sterile water and air-dried. 100 μl of Sulforhodamine B solution (SRB, Sigma, St. Louis, Mo., USA) at 0.4% (w/v) in 1% acetic acid (Fluka, Seelze, Germany) was subsequently added to each well and incubated at room temperature for 30 minutes. After staining, unbound dye was removed by 1% acetic acid and the plates were again air-dried. Bound stain in each well was solubilized with 100 μl of 10 mM trizma base (Bioshop, Burlington, ON, Canada), and the absorbance was measured using an automated plate reader (Anthos 2001, Anthos Labtec Instrument) at 540 nm.

4.3 Data Analysis

The graph and data were analyzed by SigmaPlot 10.0 software and Microsoft Excel 2002.

4.4 Results

Tables 5 and 6 show the 50% inhibitory concentration ($IC_{50}$) values for Lipotecan®, TLC388 HCl and Topotecan as well as the enhancement factor ($IC_{50\ TLC388\ HCl}/IC_{50\ Lipotecan®}$).

TABLE 5

In Vitro Cytotoxic Effect of Lipotecan ®, TLC388 HCl and Topotecan Against Selected Cancer Cell Lines

| Cell line | Incubation Time | $IC_{50}$ (μM) Topotecan | TLC388 HCl | Lipotecan ® | Ratio* |
|---|---|---|---|---|---|
| Human Hepatoma ||||||
| HepG2 | 24 h | 57.45 | 26.27 | 3.69 | 7.12 |
|  | 48 h | 2.73 | 2.33 | 0.20 | 11.65 |
|  | 72 h | 0.686 | 0.71 | 0.08 | 8.88 |
| HepG2/ | 24 h | >50 | 31.49 | 3.37 | 9.34 |
| 2.2.15 | 48 h | 63.1 | 19.36 | 1.15 | 16.83 |
|  | 72 h | 0.58 | 0.73 | 0.29 | 2.5 |
| Huh-7 | 24 h | 65.3 | 30.33 | 1.23 | 24.66 |
|  | 48 h | 5.05 | 4.41 | 0.43 | 10.26 |
|  | 72 h | 2.8 | 3.45 | 0.29 | 11.9 |
| Hep3B | 24 h | >50 | 2.98 | 3.02 | 0.99 |
|  | 48 h | 64.58 | 0.93 | 0.69 | 1.35 |
|  | 72 h | 0.2 | 0.18 | 0.08 | 2.25 |
| Sk-Hep-1 | 24 h | 74.89 | 5.50 | 1.50 | 3.67 |
|  | 48 h | 12.46 | 3.90 | 1.90 | 2.05 |
|  | 72 h | 2.10 | 0.34 | 0.16 | 2.13 |
| Prostate Cancer ||||||
| DU145 | 24 h | 2.25 | 3.07 | 0.17 | 18.06 |
|  | 48 h | 0.60 | 0.85 | 0.10 | 8.5 |
|  | 72 h | 0.58 | 0.78 | 0.06 | 13 |
| LNCap | 24 h | 14.93 | 8.17 | 8.63 | 0.95 |
|  | 48 h | 6.15 | 1.38 | 1.44 | 0.96 |
|  | 72 h | 2.59 | 0.35 | 0.23 | 1.52 |
| PC-3 | 24 h | 130.63 | 23.35 | 3.21 | 7.27 |
|  | 48 h | 18.12 | 6.73 | 1.07 | 6.29 |
|  | 72 h | 3.58 | 3.68 | 0.47 | 7.83 |
| Colon Cancer ||||||
| HCT116 | 72 h | 0.008 | 0.001 | 0.27 | 0.004 |
| HT29 | 72 h | 0.038 | 0.0006 | 0.52 | 0.001 |

NOTE:

*The $IC_{50}$ ratios are calculated to indicate enhancement in cytotoxicity of TLC388 HCl over Lipotecan ® ($IC_{50\ TLC388\ HCl}/IC_{50\ Lipotecan\ ®}$)

TABLE 6

In Vitro Cytotoxic Effect of Lipotecan®, TLC388
HCl and Topotecan in RG-2 Glioma Cell Line.

| Cell line | Incubation Time | IC$_{50}$ (μM) | | | Ratio* |
|---|---|---|---|---|---|
| | | Topotecan | TLC388 HCl | Lipotecan® | |
| RG-2 | 24 h | 7.23 | 7 | 1.23 | 5.7 |
| | 48 h | 2.78 | 2.1 | 0.53 | 4 |
| | 72 h | 3 | 2.12 | 0.24 | 8.8 |

Note:
*The IC$_{50}$ ratios are calculated to indicate enhancement in cytotoxicity of TLC388 HCl over Lipotecan® (IC$_{50\ TLC388\ HCl}$/IC$_{50\ Lipotecan}$®)

As shown in Tables 5 and 6, Lipotecan is more effective in inhibiting hepatoma, prostate and glioma cancer cells than TLC388 HCl. In addition, Lipotecan® is effective in inhibiting the colon cancer cells.

EXAMPLE 5

Bone Marrow Suppression Evaluation

Figure 3:
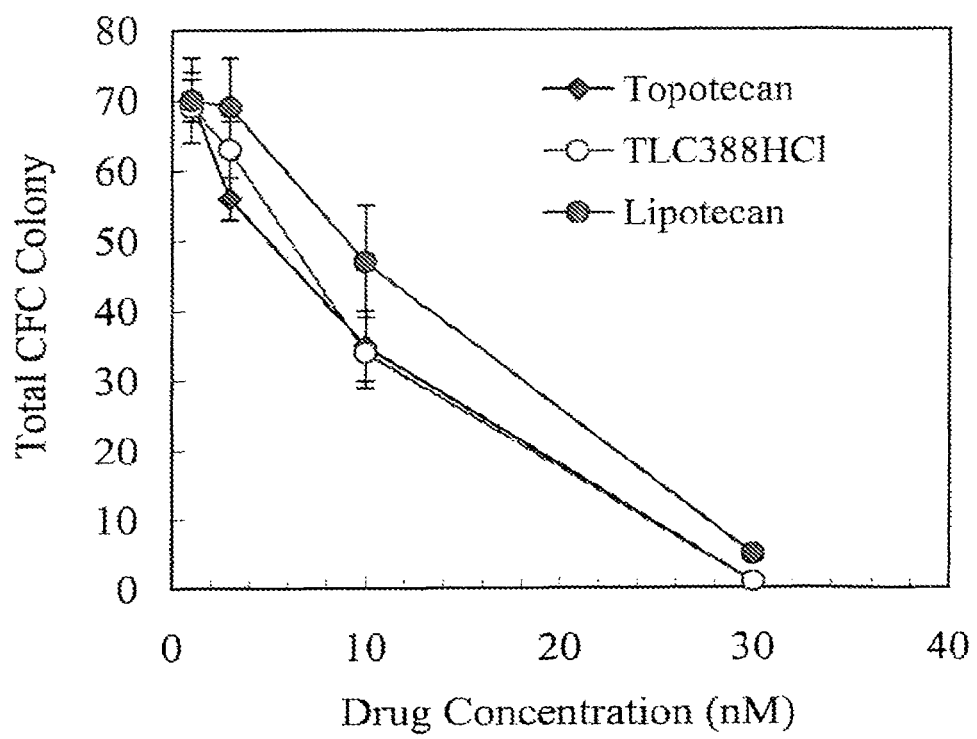
FIG. 3 shows the toxic effect of free TLC388 HCl, Topotecan and Lipotecan® on human hematopoietic progenitors.

An in vitro evaluation of the effect of the pharmaceutical compositions on human bone marrow cells was performed.
Protocol: Clonogenic progenitors of the erythroid (CFU-E, BFU-E), granulocyte-monocyte (CFU-GM) and multipotential lineages (CFU-GEMM) were set up in methylcellulose-based medium (R&D Systems) containing recombinant rhSCF (50 ng/mL), rhIL-3 (10 ng/mL), rhGM-CSF (10 ng/mL), and rhEpo (3 U/mL).
TLC388 HCl and Topotecan were diluted in DMSO and Lipotecan® was diluted in sterile water to provide the appropriate working stock concentrations. These working stock solutions were subsequently added to the methylcellulose-based colony assay medium described above. The colony assay mediums were set up in triplicate at 2×10$^4$ cells per culture medium.
The replicate culture mediums were incubated at 37° C. in 5% CO$_2$ for 14-16 days. After this time, the resultant colonies in the culture medium were evaluated by a senior scientist in term of size and morphology.
FIG. 3 shows the toxicity of TLC388 HCl, Topotecan and Lipotecan® (TLC388 HCl composition) on human erythroid and myeloid progenitor. The IC$_{50}$ values of the free TLC388 HCl were 9.3 nM for erythroid Colony Forming Cells (CFCs) and 9.8 nM for myeloid CFCs. The IC$_{50}$ values of Topotecan were 11.8 nM for erythroid CFCs and 8.7 nM for myeloid CFCs. The IC$_{50}$ values of Lipotecan® were 12.5 nM for erythroid CFCs and 11.5 nM for myeloid CFCs. The results show that the toxic effects of Lipotecan® on human erythroid and myeloid progenitors were lower than that of free TLC388 HCl and Topotecan.
This data indicates that Lipotecan® composition of the present invention has increased anti-cancer effect to various cancer cell lines, such as hepatoma, prostate cancer and glioma cell lines, and lower toxicity on bone marrow cells such as erythroid and myeloid CFCs.
When ranges are used herein for physical properties, such as molecular weight, or chemical properties, such as chemical formulae, all combinations, and subcombinations of ranges specific embodiments therein are intended to be included.
Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of using a topoisomerase I inhibitor in treatment of cancer to reduce bone marrow suppression, comprising:
   administering to a subject in need thereof an effective amount of a pharmaceutical composition that comprises:
   at least one hydrophobic topoisomerase I inhibitor or a pharmaceutically acceptable salt thereof; and
   at least one polyethylene glycol (PEG) conjugated phospholipid;
   wherein the molar ratio of said PEG conjugated phospholipid to said hydrophobic topoisomerase I inhibitor or said pharmaceutically acceptable salt of said hydrophobic topoisomerase I inhibitor is about 0.45:1 to about 1.05:1.

2. The method of claim 1, wherein said hydrophobic topoisomerase I inhibitor is selected from the group consisting of: an acridine compound, an actinomycin, an anthracycline compound, an anthraquinone compound, a berberine alkaloid, a benzofluoranthene compound, a benzophenanthridine alkaloid, a camptothecin derivative, a DNA minor groove binder, an indolocarbazole compound, a naphthoquinone compound, a flavonoid, a quinoline compound, a terbenzimidazole compound, and a tricyclic carboxamide derivative.

3. The method of claim 1, wherein said hydrophobic topoisomerase I inhibitor is selected from the group consisting of: aclacinomycin A, 5-acridin-9-ylmethylidene-3-amino-2-thioxothiazolidin-4-one, 5-acridin-9-ylmethylidene-2-thioxoimidazolidin-4-one, 3-acridin-9-ylmethylthiazolidine-2,4-dione, silatecan, 9-aminocamptothecin, gimatecan, karenitecin, diflomotecan, rubitecan, 7-ethylcamptothecin, 10-aminocamptothecin, 10,11-methylenedioxycamptothecin, 9-amino-10,11-methylenedioxycamptothecin, 9-chloro-10,11-methylenedioxycamptothecin, TLC388, TLC1988, actinomycin D, NU/ICRF 505, epiberberine, coralyne, beta-lapachone, nitidine, fagaronine, corilagin, rebeccamycin, KT6006, KT6528, ED-110, NB-506, alkannin, shikonin, EMD 21388, EMD 50689, acacetin, kaempferol, saintopin, 5-phenyl-terbenzimidazole (5PTB), topostatin, topostin B567, and intoplicine.

4. The method of claim 1, wherein said hydrophobic topoisomerase I inhibitor is a compound having a water solubility less than camptothecin.

5. The method of claim 4, wherein said hydrophobic topoisomerase I inhibitor is a compound having a water solubility less than 0.511 mg/mL.

6. The method of claim 1, further comprising at least one pH adjusting agent.

7. The method of claim 1, further comprising at least one pharmaceutically acceptable excipient or carrier.

8. The method of claim 1, wherein the molar ratio of said PEG conjugated phospholipid to said hydrophobic topoisomerase I inhibitor or said pharmaceutically acceptable salt of said hydrophobic topoisomerase I inhibitor is about 0.60:1 to about 1.00:1.

9. The method of claim 1, wherein said pharmaceutical composition has a pH less than about 4.

10. The method of claim 1, wherein the PEG conjugated phospholipid comprises a PEG moiety having a molecular weight from about 1,000 to about 20,000 daltons conjugated to a phospholipid moiety.

11. The method of claim 1, wherein the PEG conjugated phospholipid is a PEG-DSPE conjugate.

12. The method of claim 1, wherein the hydrophobic topoisomerase I inhibitor or the pharmaceutically acceptable salt of said hydrophobic topoisomerase I inhibitor and PEG conjugated phospholipid form micelles with a size less than about 40 nm.

13. The method of claim 1, wherein the hydrophobic topoisomerase I inhibitor comprises one or more electron-affinic moieties being directly or indirectly attached to one of the carbons at the $C_5$, $C_7$, $C_9$, $C_{10}$, $C_{11}$, $C_{12}$ or $C_{20}$ position of camptothecin.

14. The method of claim 1, wherein the hydrophobic topoisomerase I inhibitor is a camptothecin derivative having a planar pentacyclic ring structure.

15. The method of claim 13, wherein said camptothecin derivative is selected from the group consisting of: silatecan, 9-aminocamptothecin, gimatecan, karenitecin, diflomotecan, rubitecan, 7-ethylcamptothecin, 10-aminocamptothecin, 10,11-methylenedioxycamptothecin, 9-amino-10,11-methylenedioxycamptothecin, 9-chloro-10,11-methylenedioxycamptothecin, TLC388, and TLC1988.

16. The method of claim 6, wherein the pH adjusting agent is tartaric acid or citric acid.

17. The method of claim 1, wherein the molar ratio of said PEG conjugated phospholipid to said hydrophobic topoisomerase I inhibitor or said pharmaceutically acceptable salt of said hydrophobic topoisomerase I inhibitor is about 0.70:1 to about 0.90:1.

18. The method of claim 11, wherein the PEG-DSPE conjugate is a methoxyl PEG-DSPE conjugate.

* * * * *